United States Patent
Cohn et al.

(10) Patent No.: US 6,465,463 B1
(45) Date of Patent: Oct. 15, 2002

(54) METHODS OF TREATING AND PREVENTING CONGESTIVE HEART FAILURE WITH HYDRALAZINE COMPOUNDS AND ISOSORBIDE DINITRATE OR ISOSORBIDE MONONITRATE

(75) Inventors: Jay N. Cohn, Minneapolis, MN (US); Peter Carson, Chevy Chase, MD (US)

(73) Assignee: NitroMed, Inc., Bedford, MA (US)

(*) Notice: Subject to any disclaimer, the term of this patent is extended or adjusted under 35 U.S.C. 154(b) by 0 days.

(21) Appl. No.: 09/658,261

(22) Filed: Sep. 8, 2000

Related U.S. Application Data

(60) Provisional application No. 60/152,616, filed on Sep. 8, 1999, and provisional application No. 60/171,102, filed on Dec. 16, 1999.

(51) Int. Cl.$^7$ .......................... A61K 31/50; A61K 31/34
(52) U.S. Cl. ........................................ 514/248; 514/470
(58) Field of Search .................................. 514/248, 470

(56) References Cited

U.S. PATENT DOCUMENTS

| | | | |
|---|---|---|---|
| 4,868,179 A | 9/1989 | Cohn | |
| 5,627,191 A | 5/1997 | Birch et al. | |
| 5,645,839 A | 7/1997 | Chobanian et al. | |
| 5,891,459 A | 4/1999 | Cooke et al. | |
| 5,968,983 A | 10/1999 | Kaesemeyer | |
| 5,973,011 A | 10/1999 | Noack et al. | |
| 6,103,769 A | 8/2000 | Kelm | |
| 6,117,872 A | 9/2000 | Maxwell et al. | |

FOREIGN PATENT DOCUMENTS

| | | |
|---|---|---|
| WO | WO 95/26725 | 3/1994 |
| WO | WO 98/21193 | 5/1998 |
| WO | WO 99/66921 | 6/1998 |
| WO | WO 99/00361 | 1/1999 |
| WO | WO 99/67231 | 12/1999 |

OTHER PUBLICATIONS

Dupuis, Cardiovascular Drugs and Therapy, 8(3):501–507 (1994) (entire journal article).
Freedman et al, Drugs, 54(Supplement 3): 41–50 (1997).
Sherman et al, Cardiologia, 42(2):177–187 (1997).
Biegelson et al, Coronary Artery Disease, 10:241–256 (1999).
Rudd et al, Am. J. Physiol., 277(46):H732–H739 (1999).
Hammerman et al, Am. J. Physiol., 277(46):H1579–1592 (1999).
Loscalzo et al, Transactions of the American and Climatological Ass., 111:158–163 (2000).
Cohn et al, The New England Journal of Medicine, 325(5):303–310 (1991).
Cohn et al, The New England Journal of Medicine, 314(24):1547–1552 (1986).
Carson et al, Circulation, Supplement I, 92(8):I31–I32, Abstract No. 0145 (1995).
Francis et al, Circulation, Supplement VI, 87(6):V140–V148 (1993).
Pierpont et al, Chest, 73(1):8–13 (1978).
Massie et al, The American Journal of Cardiology, 40:794–801 (1977).
Kaplan et al, Annals of Internal Medicine, 84:639–645 (1976).
Bauer et al, Circulation, 84(1):35–39 (1991).
The SOLVD Investigators, The New England Journal of Medicine, 327(10):685–691 (1992).
Ziesche et al, Circulation, 87(6):VI56–VI64 (1993).
Rector et al, Circulation, 87(6):VI71–VI77 (1993).
Carson et al, Journal of Cardiac Failure, 5(3):178–187 (Sep. 10, 1999).
Dries et al, The New England Journal of Medicine, 340(8):609–616 (Feb. 25, 1999).

*Primary Examiner*—Raymond Henley, III
(74) *Attorney, Agent, or Firm*—Hale and Dorr LLP

(57) ABSTRACT

The present invention provides methods or treating and preventing mortality associated with heart failure in an African American patient with hypertension and improving oxygen consumption, quality of life and exercise tolerance by administering a therapeutically effective amount of at least one hydralazine compound and at least one of isosorbide dinitrate and isosorbide mononitrate, and, optionally, one or more compounds, such as, for example, a digitalis, a diuretic compound, or a compound used to treat cardiovascular diseases. In the present invention, the hydralazine compound is preferably hydralazine or a pharmaceutically acceptable salt thereof. Preferred methods of the invention comprise administering hydralazine or a pharmaceutically acceptable salt thereof and isosorbide dinitrate.

54 Claims, 14 Drawing Sheets

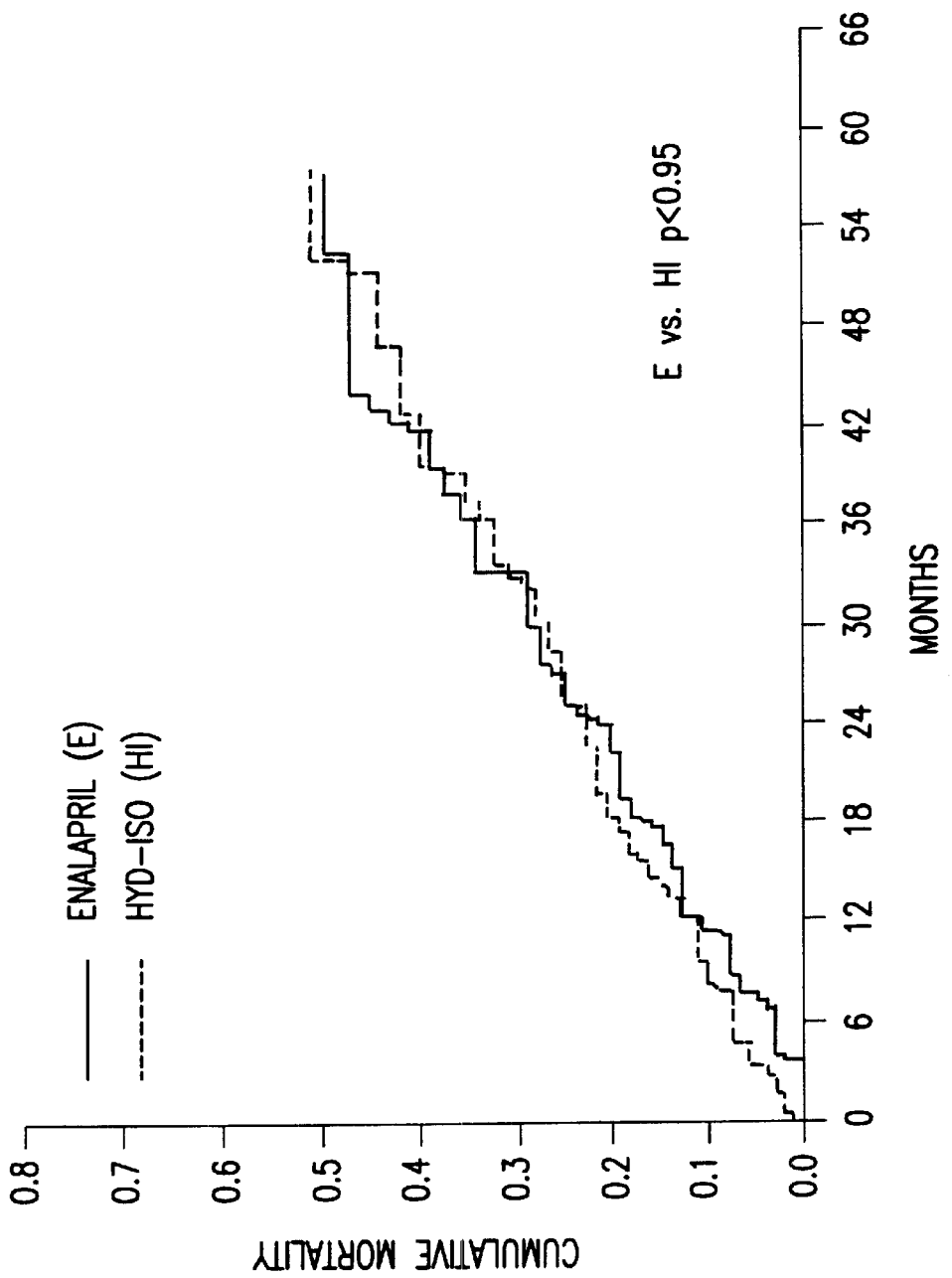

METHODS OF TREATING AND PREVENTING CONGESTIVE HEART FAILURE WITH HYDRALAZINE COMPOUNDS AND ISOSORBIDE DINITRATE OR ISOSORBIDE MONONITRATE

RELATED APPLICATIONS

This application claims priority to U.S. Provisional Application No. 60/152,616 filed Sep. 8, 1999, and U.S. Provisional Application No. 60/171,102 filed Dec. 16, 1999.

FIELD OF THE INVENTION

The present invention provides methods of treating and preventing mortality associated with heart failure, improving oxygen consumption, quality of life and/or exercise tolerance in a black patient, with hypertension by administration of a therapeutically effective amount of at least one hydralazine compound or a pharmaceutically acceptable salt thereof, and at least one of isosorbide dinitrate and isosorbide mononitrate, and, optionally, one or more compounds, such as, for example, a digitalis, a diuretic compound, and/or a compound used to treat cardiovascular diseases.

BACKGROUND OF THE INVENTION

Heart failure in black patients has been associated with a poorer prognosis than in white patients. In diseases such as hypertension, blacks exhibit pathophysiologic differences and respond differently to some therapies than whites.

Congestive heart failure (CHF) is a clinical syndrome involving cardiac and peripheral abnormalities that produce morbidity and shortened life span. This syndrome is now the leading cause of hospitalization in individuals older than age 65 and is a major contributor to the escalation of heath care costs. Recent reports by Ghali et al (*Arch. Intern. Med.* 150:769–773 (1990)) and Alexander et al (*JAMA*, 274(13):1037–1042 (1995)) have suggested that black patients may have a greater risk than white patients of developing heart failure that consumes medical resources (Whittle et al., *N. Engl. J. Med.*, 329:621–627 (1993)), and the population-based mortality rate for heart failure has been reported to be significantly higher in blacks (Gillum, *Am. Heart J.*, 113: 1043–1045 (1987)).

Vasodilator-Heart Failure Trials (V-HeFT) have been conducted, and the trials' designs and results have been published previously (Cohn et al, *N. Engl. J. Med.*, 314:1547–1552 (1986); Cohn et al, *N. Engl. J. Med.* 325:303–310 (1991)). V-HeFT I was conducted between 1980 and 1985, prior to the introduction of ACE inhibitor therapy. V-HeFT II was conducted from 1985 to 1990. V-HeFT I and V-HeFT II did not consider the race or ethnic origin of the patients that participated in the studies.

Cardiovascular disease may, however, affect white and black patients differently. For example, hypertension, a major etiology of heart failure in black patients, differs pathophysiologically and in treatment response between racial groups (Gillum, *Hypertension*, 1:468–475 (1979)). No data at present have examined whether similar differences exist between black patients and white patients with heart failure.

There is a need in the art for new and more effective compositions and methods for treating and preventing mortality associated with heart failure in black patients with hypertension. The present invention is directed to these, as well as other, important ends.

SUMMARY OF THE INVENTION

The present invention provides methods for treating and preventing mortality associated with heart failure, improving oxygen consumption, quality of life and/or exercise tolerance in non-Caucasian patients, preferably black patients, with hypertension by administering a therapeutically effective amount of at least one hydralazine compound or a pharmaceutically acceptable salt thereof, and at least one of isosorbide dinitrate and isosorbide mononitrate, and, optionally, one or more compounds, such as, for example, a digitalis, a diuretic compound, and/or a compound used to treat cardiovascular diseases. The hydralazine compound is preferably hydralazine, or a pharmaceutically acceptable salt thereof, such as hydralazine hydrochloride. The hydralazine compound and the isosorbide dinitrate or isosorbide mononitrate can be administered separately or as components of the same composition.

These and other aspects of the present invention are described in more detail below.

BRIEF DESCRIPTION OF THE FIGURES

FIG. 2A shows the benefit of hydralazine-isosorbide dinitrate in black patients (HI) (placebo, n=79; HI, n=49; prazosin, n=52); FIG. 2B shows an absence of demonstrable treatment benefit in white patients (placebo, n=192; HI, n=132; prazosin, n=127).

FIGS. 3A–3B shows the racial difference in the effect of treatment on mortality in V-HeFT II. FIG. 3A shows that enalapril and hydralazine-isosorbide dinitrate exhibit similar survival curves in black patients (enalapril, n=106; HI, n=109); FIG. 3B shows that enalapril exerts significant survival benefit in white patients (enalapril, n=292; HI, n=282).

FIG. 4A and FIG. 4B show the mortality of white patients with and without a hypertensive history, respectively. FIG. 4C and FIG. 4D show the mortality of black patients with and without a hypertensive history, respectively. The benefit of enalapril compared to hydralazine-isosorbide dinitrate was most apparent in white patients with a hypertensive history. Details of the patient population are shown in Table 3.

DETAILED DESCRIPTION OF THE INVENTION

Figure 1:
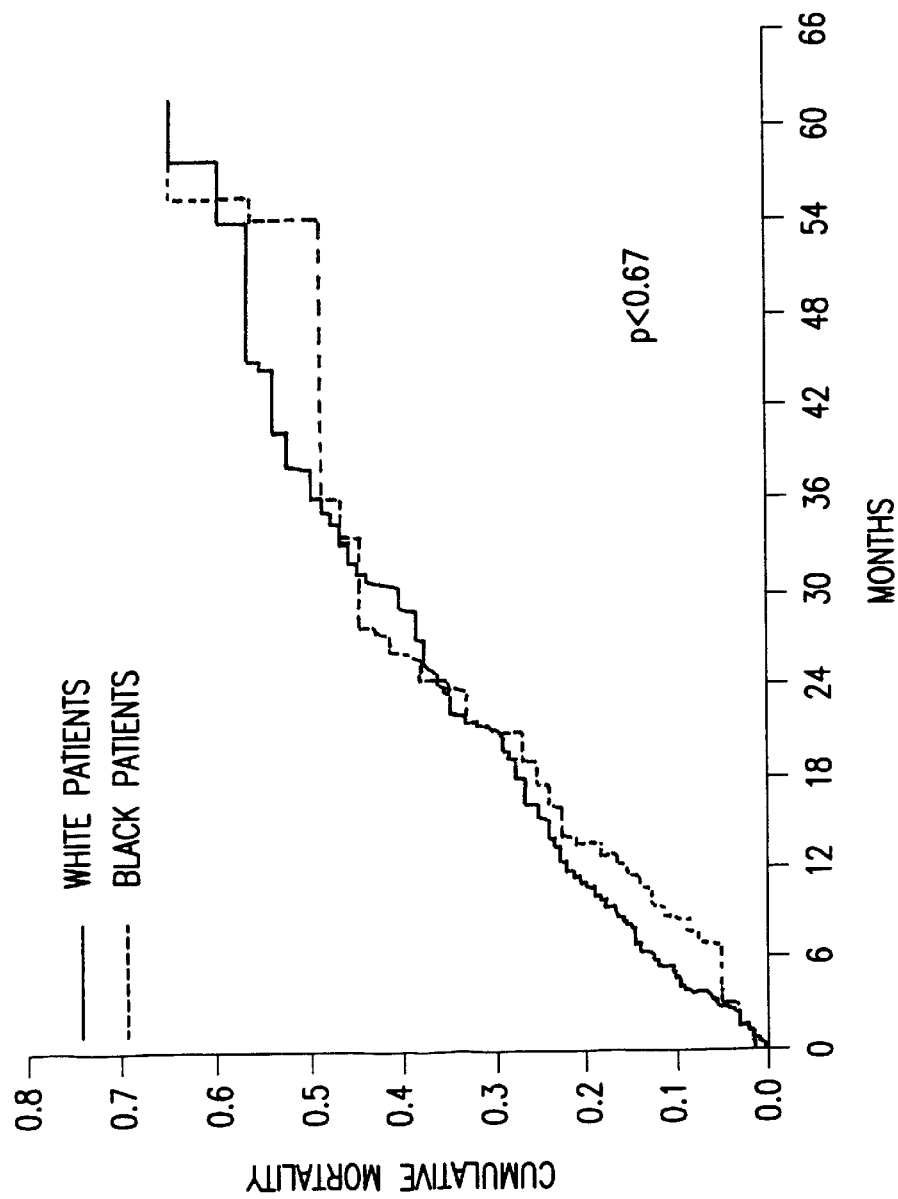
FIG. 1 shows the racial difference in mortality in the placebo group in V-HeFT I. White and black patients exhibited similar survival (White, n=192; Black, n=79).

In the present invention, the results of the first Vasodilator-Heart Failure Trial (V-HeFT I) were reexamined and reevaluated, and the baseline characteristics, prognosis, and response to therapy for 180 black male patients and 450 white male patients were compared. V-HeFT II was also reexamined and reevaluated in the present invention, and the same comparisons were made for 215 black male patients and 574 white male patients, including an analysis stratified by the presence or absence of a history of hypertension. It has now been discovered that in both V-HeFT I and II, black patients had a lower incidence of coronary artery disease, more previous hypertension, and a larger cardiothoracic ratio (p<0.05) than white patients. In V-HeFT II, plasma norepinephrine was significantly lower in blacks; and plasma renin activity was lower only in blacks with a history of hypertension. Overall mortality or congestive heart failure hospitalization did not differ between blacks and whites in the placebo group in V-HeFT I.

It has now been unexpectedly discovered that the mortality of black patients is significantly reduced, and that their oxygen consumption, quality of life and/or exercise tolerance are improved by the administration of at least one hydralazine compound or a pharmaceutically acceptable salt thereof and at least one of isosorbide dinitrate and isosorbide mononitrate, and, optionally, one or more compounds, such as, for example, a digitalis, a diuretic compound, and/or other compounds used to treat cardiovascular diseases. With the administration of the hydralazine compound (e.g., hydralazine), and isosorbide dinitrate the mortality of black patients was significantly reduced (p=0.04) in V-HeFT I, whereas white patients showed no difference from placebo. In V-HeFT II, only white patients exhibited a mortality reduction from enalapril compared to the combination of hydralazine and isosorbide dinitrate (p=0.02). Whites also showed evidence of greater blood pressure reduction and enhanced regression of cardiac size in response to enalapril. When stratified by history of hypertension in V-HeFT II, only whites with a history of hypertension, who had higher renin levels, showed significant mortality reduction with enalapril compared to the combination of hydralazine and isosorbide dinitrate. Hospitalization rate did not differ between any treatment group in either study.

Black and white patients exhibit differences in etiology, neurohormonal stimulation and pharmacologic response in heart failure. The present invention reveals that angiotensin-converting enzyme (ACE) inhibitors are unexpectedly superior in treating white patients, and that the administration of at least one hydralazine compound and at least one of isosorbide dinitrate and isosorbide mononitrate is unexpectedly superior in treating African American patients. For example, the patient can be administered a hydralazine compound and isosorbide dinitrate, or the patient can be administered a hydralazine compound and isosorbide mononitrate, or the patient can be administered a hydralazine compound, isosorbide dinitrate and isosorbide mononitrate. Preferably, the patient is administered a hydralazine compound and isosorbide dinitrate.

This invention for the first time analyzes the baseline characteristics and prognosis of a well-defined population of black and white patients based on Vasodilator-Heart Failure Trials (V-HeFT I and II) (Cohn et al, *N. Engl. J. Med.*, 314:1547–1552 (1986); Cohn et al, *N. Engl. J. Med.* 325:303–310 (1991)). Furthermore, since the clinical response of black hypertensive patients to therapy such as angiotensin-converting enzyme (ACE) inhibitors has differed from whites (*Br. J. Clin. Pharmac.*, 14 (Suppl S):97–101 (1982); Saunders et al, *Arch. Intern. Med.*, 150:1710–1713 (1990)) the inventors now, for the first time, considered and analyzed differences in the racial response to the specific therapies within these studies.

The following definitions are used throughout the specification.

"Patient" refers to animals, preferably mammals, most preferably humans, and includes males and females.

"Black" refers to a person of African descent or an African-American person.

"Therapeutically effective amount" refers to the amount of the compound and/or composition that is effective to achieve its intended purpose.

"Hydralazine compound" refers to a compound having the formula:

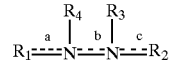

wherein a, b and c are each independently a single or a double bond; $R_1$ and $R_2$ are each independently a hydrogen, an alkyl, an ester or a heterocyclic ring; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine and the like.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6 dioxabicyclo[3.3.0] octane, 7-oxabycyclo[2.2.1]heptyl, 8-azabicyclo[3,2,1]oct-2-enyl and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, arylcarboxamido, hydrazino, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3, 5-trithianyl, benzo(b)thiophenyl, benzimidazolyl, quinolinyl, and the like.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Hydroxy" refers to —OH.

"Hydroxyalkyl" refers to a hydroxy group, as defined herein, appended to an alkyl group, as defined herein.

"Alkylcarbonyl" refers to $R_{52}$-C(O)—, wherein $R_{52}$ is an alkyl group, as defined herein.

"Arylcarbonyl" refers to $R_{52}$-C(O)—, wherein $R_{55}$ is an aryl group, as defined herein.

"Ester" refers to $R_{51}$C(O)O— wherein $R_{51}$ is a hydrogen atom, an alkyl group, an aryl group, an alkylaryl group, or an arylheterocyclic ring, as defined herein.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Hydrazino" refers to $H_2N$—N(H)—.

"Oxygen consumption" was measured during a progressive maximal bicycle-ergometer exercise test taken while the expired air was collected continuously to monitor oxygen consumption. Dyspnea or fatigue occurred at a peak oxygen consumption of <25 ml per kilogram of body weight per minute. Patients with pulmonary diseases, obstructive valvular diseases and the like, tend to have a low oxygen consumption. An increase in a patient's oxygen consumption typically results in the patient's increased exercise tolerance and implies that the patient would have an improved quality of life.

"Quality of life" refers to one or more of a persons ability to walk, climb stairs, do errands, work around the house, participate in recreational activities, and/or not requiring rest during the day, and/or the absence of sleeping problems or shortness of breath. The quality of life was measured using the Heart Condition Assessment (HCA) questionnaire. The questionnaire was self-administered after brief standardization instructions. The score was obtained by summing the ranks of the responses to each question.

"Compound used to treat a cardiovascular disease" refers to any therapeutic compound used to treat any cardiovascular disease. Suitable compounds include, but are not limited to, angiotensin-converting enzyme (ACE) inhibitors (such as, for example, alacepril, benazepril, captopril, ceronapril, cilazapril, delapril, duinapril, enalapril, enalaprilat, fosinopril, imidapril, lisinopril, moveltipril, pentopril, perindopril, quinapril, ramipril, rentiapril, spirapril, temocapril, trandolapril, zofenopril, and the like); beta-adrenergic blockers (such as, for example, amosulalol, atenolol, betaxolol, bethanoline, bevantolol, bisoprolol, bopindolol, bucindolol, bufuralol, bunitrolol, bupranolol, butafilolol, carazolol, carteolol, carvedilol, celiprolol, cetamolol, dilevalol, epanolol, indenolol, mepindolol, metipranolol, metoprolol, moprolol, nadolol, nebivolol, nipradilol, penbutolol, pindolol, pronethalol, propranolol, sotalol, sulfinalol, talinolol, tertatolol, tilisolol, timolol, toliprolol, and the like); cholesterol reducers (such as, for example, lovastatin (MEVACOR®), simvastatin (ZOCOR®), pravastatin (PRAVACHOL®), fluvastatin, cerivastatin (BAYCOL®), atorvastatin (LIPITOR®), and the like); calcium channel blockers (such as, for example, amlodipine, aranidipine, bamidipine, benidipine, cilnidipine, clentiazem, diltiazen, efonidipine, fantofarone, felodipine, isradipine, lacidipine, lercanidipine, manidipine, mibefradil, nicardipine, nifedipine, nilvadipine, nisoldipine, nitrendipine, semotiadil, veraparmil, and the like); angiotensin II receptor antagonists (such as, for example, ciclosidomine, eprosartan, furosemide, irbesartan, losartan, saralasin, valsartan, and the like); endothelin antagonists (such as, for example, bosentan, sulfonamide endothelin antagonists, BQ-123, SQ 28608, and the like); and mixtures thereof. The preferred compound used to treat cardiovascular diseases is enalapril.

"Cardiovascular diseases" refers to any cardiovascular disease, including but not limited to, congestive heart failure, hypertension, pulmonary hypertension, myocardial and cerebral infarctions, atherosclerosis, atherogenesis, thrombosis, ischemic heart disease, post-angioplasty restenosis, coronary artery diseases, renal failure, stable, unstable and variant (Prinzmetal) angina, atherosclerosis, cardiac edema, renal insufficiency, nephrotic edema, hepatic edema, stroke, and the like.

In the present invention, the preferred hydralazine compound is hydralazine, which is preferably administered in the form of a pharmaceutically acceptable salt and most preferably in the form of hydralazine hydrochloride. Hydralazine hydrochloride is commercially available from, for example, Lederle Standard Products, Pearl River, N.Y.; and Par Pharmaceuticals Inc., Spring Valley, N.Y.

Isosorbide dinitrate is commercially available, for example, under the trade names DILATRATE®-SR (Schwarz Pharma, Milwaukee, Wis.); ISORDIL® and ISORDILR TITRADOSE® (Wyeth Laboratories Inc., Philadelphia, Pa.); and SORBITRATE® (Zeneca Pharmaceuticals, Wilmington, Del.).

Isosorbide mononitrate is commercially available, for example, under the trade names IMDUR® (A. B. Astra, Sweden); MONOKET® (Schwarz Pharma, Milwaukee, Wis.); and ISMO® (Wyeth-Ayerst Company, Philadelphia, Pa.).

The isosorbide dinitrate and isosorbide mononitrate can be stabilized to prevent explosions by the addition of compounds, such as, but not limited to, lactose, arginine, and the like, and mixtures thereof.

The hydralazine compound and at least one of isosorbide dinitrate and isosorbide mononitrate can be administered as separate components or as components of the same composition. When the hydralazine compound and at least one of isosorbide dinitrate and isosorbide mononitrate are administered as separate components, they are preferably administered to the patient at about the same time. "About the same time" means that within about thirty minutes of administering one compound (e.g., the hydralazine compound or isosorbide dinitrate/mononitrate) to the patient, the other compound (e.g., isosorbide dinitrate/mononitrate or the hydralazine compound) is administered to the patient. "About the same time" also includes simultaneous administration of the compounds.

In addition to the administration of the combination of hydralazine compound and at least one of isosorbide dinitrate and isosorbide mononitrate for the treatment of heart failure, and/or for improving oxygen consumption, quality of life and/or exercise tolerance, the patients can also be administered digitalis, such as, for example, digoxin, and/or diuretics and/or a compound used to treat cardiovascular diseases. The digoxin is administered preferably orally to achieve a steady state blood serum concentration of at least about 0.7 nanograms per ml to about 2.0 nanograms per ml. The diuretic is administered, preferably orally, to manage edema. Suitable diuretics include, but are not limited to, thiazides (such as, for example, chlorothiazide, hydrochlorothiazide), ethacrynic acid, furosemide, spironalactone, triamterene or mixtures thereof. Depending on the diuretic employed, potassium may also be administered to the patient in order to optimize the fluid balance while avoiding hypokalemic alkalosis. The administration of potassium can be in the form of potassium chloride or by the daily ingestion of foods with high potassium content such as, for example, bananas or orange juice. The method of administration of these compounds is described in further detail in U.S. Pat. No. 4,868,179, the disclosure of which is incorporated by reference herein in its entirety.

The compounds and compositions of the present invention can be administered by any available and effective delivery system including, but not limited to, orally, bucally, parenterally, by inhalation spray, or rectally in dosage unit formulations containing conventional nontoxic pharmaceutically acceptable carriers, adjuvants, and vehicles as desired. The preferred methods of administration are by oral administration.

Solid dosage forms for oral administration can include capsules, tablets, chewable tablets, effervescent tablets, pills, powders, granules and gels. In such solid dosage forms, the active compounds can be admixed with at least one inert diluent such as sucrose, lactose or starch. Such dosage forms can also comprise, as is normal practice, additional substances other than inert diluents, e.g., lubricating agents, such as magnesium stearate. In the case of capsules, tablets, effervescent tablets, and pills, the dosage forms can also comprise buffering agents. Soft gelatin capsules can be prepared to contain a mixture of the active compound or composition and vegetable oil. Hard gelatin capsules can contain granules of the active compound in combination with a solid, pulverulent carrier, such as lactose, saccharose, sorbitol, mannitol, potato starch, corn starch, amylopectin, or cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for administration of the compounds or compositions can be prepared by mixing the drug with a suitable nonirritating excipient such as cocoa butter and polyethylene glycols which are solid at room temperature but liquid at body temperature, such that they will melt in the body and release the drug.

The term parenteral includes subcutaneous injections, intravenous, intramuscular, intrasternal injection, or infusion techniques. Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitrous (nitrite salt), nitric (nitrate salt), carbonic, sulfuric, phosphoric acid, and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet and medical condition of the patient, the severity of the cardiovascular disease, the route of administration, pharmacological considerations such as the activity, efficacy, pharmacokinetic and toxicology profiles of the particular compound used, whether a drug delivery system is used, and whether the compound is administered as part of a drug combination.

In preferred embodiments, the hydralazine hydrochloride is administered in an amount of about 30 milligrams per day to about 300 milligrams per day; the isosorbide dinitrate is administered in an amount of about 20 milligrams per day to about 200 milligrams per day; and the isosorbide mononitrate is administered in an amount of about 10 milligrams per day to about 120 milligrams per day. The preferred amounts of hydralazine hydrochloride, isosorbide dinitrate or isosorbide mononitrate can be administered as a single dose once a day; in multiple doses several times throughout the day; or in a sustained-release formulation.

The amount of a given compound of the present invention which will be effective will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The present invention also provides pharmaceutical kits comprising one or more containers filled with one or more of the ingredients of the pharmaceutical compounds and/or compositions. Such kits can also include, for example, other compounds and/or compositions (e.g., diuretics, digoxin, compounds used to treat cardiovascular diseases and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

Statistical Methods

Baseline measurements were restricted to the test done at the time of randomization. Change in measurements from baseline were compared between black and white patients using t-tests performed for each scheduled follow-up. Kaplan-Meier cumulative mortality curves were plotted to the end of follow-up to describe the trends in mortality over time for black and white patients. Survival curves were compared by the log-rank test. Survival in black and white patients was further analyzed by presence or absence of a history of hypertension.

In the present invention, an interaction analysis between race and treatment was performed for both V-HeFT I and II, adjusting for baseline imbalances.

Male patients were screened for participation in the study on the basis of a history of heart failure or documentation of left ventricular enlargement or dysfunction by chest radiography, echocardiography or radionuclide ventriculography. The specific ventricular imaging requirement for entry was one of the following: a radiographic cardiothoracic ratio >0.55, an echocardiographic left ventricular end-diastolic diameter >2.7 cm/m$^2$ body surface area or radionuclide left ventricular ejection fraction <0.45. In addition, patients were eligible for entry only if they had reduced maximal exercise tolerance. This was defined as a measured peak oxygen consumption ($VO_2$)<25 ml/kg per min during a progressive bicycle ergometer exercise test.

Further details of the V-HeFT trials design, conduct and results have been published previously (Cohn et al, *N. Engl. J. Med.*, 314:1547–1552 (1986); Cohn et al, *N. Engl. J. Med.* 325:303–310 (1991)). V-HeFT I was conducted between 1980 and 1985, prior to the introduction of ACE inhibitor therapy. V-HeFT II was conducted from 1985 to 1990. In patients entering V-HeFT II, a venous blood sample was obtained for measurement of plasma norepinephrine (PNE) and plasma renin activity (PRA) (Core Laboratory, University of Minnesota, Minneapolis, Minn.) after the patient had rested supine for at least 30 minutes. PNE was measured by radioenzymatic assay (Passon et al, *Anal. Biochem.*, 51:618–631 (1973)) and PRA by radioimmunoassay (Sealy et al, *Kidney Int'l.*, 240–253 (1992)).

Nearly all patients were receiving background therapy with diuretic and/or digoxin. They were randomized to receive placebo or active drug in V-HeFT I and either of two active drugs in V-HeFT II. Full doses of the vasodilator regimens in V-HeFT I were prazosin 5 mg four times daily, the combination of hydralazine 75 mg and isosorbide dinitrate 40 mg four times daily, or placebo. The V-HeFT II participants received either the same combination of hydralazine and isosorbide dinitrate, (H-I) regimen or enalapril 10 mg twice daily. Drug administration was double-blind. All patients were studied for the duration of the trial and for a minimum of 6 months or until death.

RESULTS

In V-HeFT I, 642 male patients with predominantly New York Heart Association class II–III heart failure were enrolled. There were 180 black patients and 450 white patients with complete baseline data. V-HeFT II enrolled 804 male patients with 215 black patients and 574 white patients having complete baseline data.

Baseline Characteristics

Demographics

Baseline characteristics in V-HeFT I are indicated in Table 1. In comparison to white patients, black patients were younger with less history of coronary artery disease (CAD). Black patients more commonly had a history of hypertension (p<0.05) and a larger cardiothoracic ratio (CTR) (p<0.01). Baseline characteristics in V-HeFT II are shown in Table 2. Black patients again less commonly had a history of CAD and more commonly a history of hypertension (p<0.01) than white patients. They also had lower functional capacity ($MVO_2$) and larger CTR (p<0.05).

Neurohormones

Neurohormonal activation was measured in V-HeFT II. Due to the wide range of values which produced a skewed distribution, values are expressed as medians with confidence intervals. Plasma renin activity (PRA) in white patients overall did not differ significantly from that of black patients, (7.3 ng/ml/hr [3.9–17.7] vs 6.55 ng/ml/hr [3.4–12.7] (p=0.10). White patients had higher plasma norepinephrine (PNE) than black patients (504[368–693] vs 449[330–602] pg/ml, p<0.003).

Since PRA has been noted to differ by race in hypertensive patients, we analyzed baseline characteristics including PRA and PNE in V-HeFT II by race in patients with and without a hypertensive history (Table 3). Both black and white patients with a hypertensive history had higher ejection fractions and higher systolic and diastolic blood pressure than patients without a hypertensive history (p<0.02). White patients with a history of hypertension had a higher PRA than black patients with a hypertensive history in analysis of median values (p=0.02). PNE did not differ.

MORTALITY

Figure 2A:
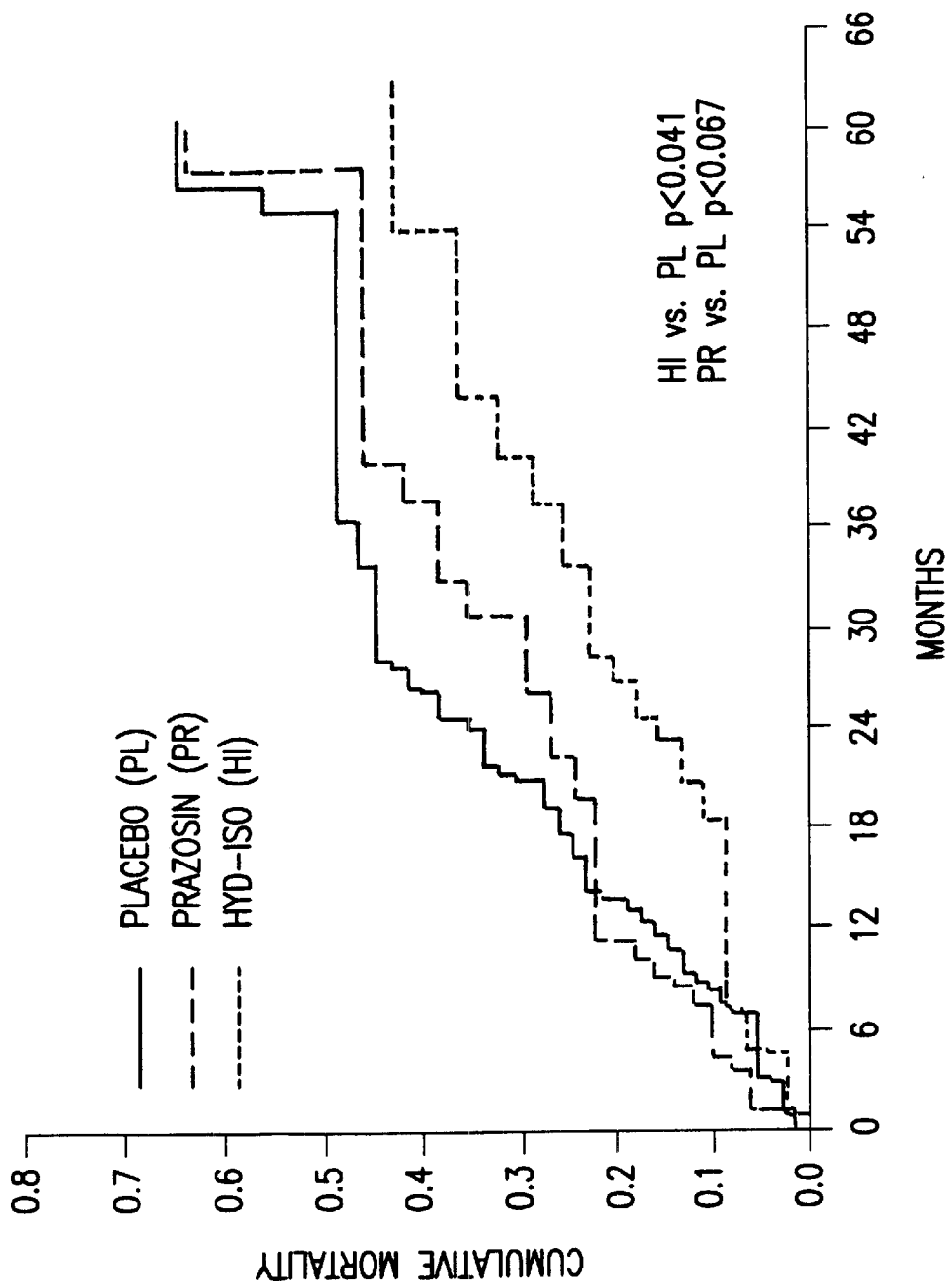
FIGS. 2A–2B shows the effects of treatment with hydralazine and isosorbide dinitrate on survival in V-HeFT I.
Figure 2B:
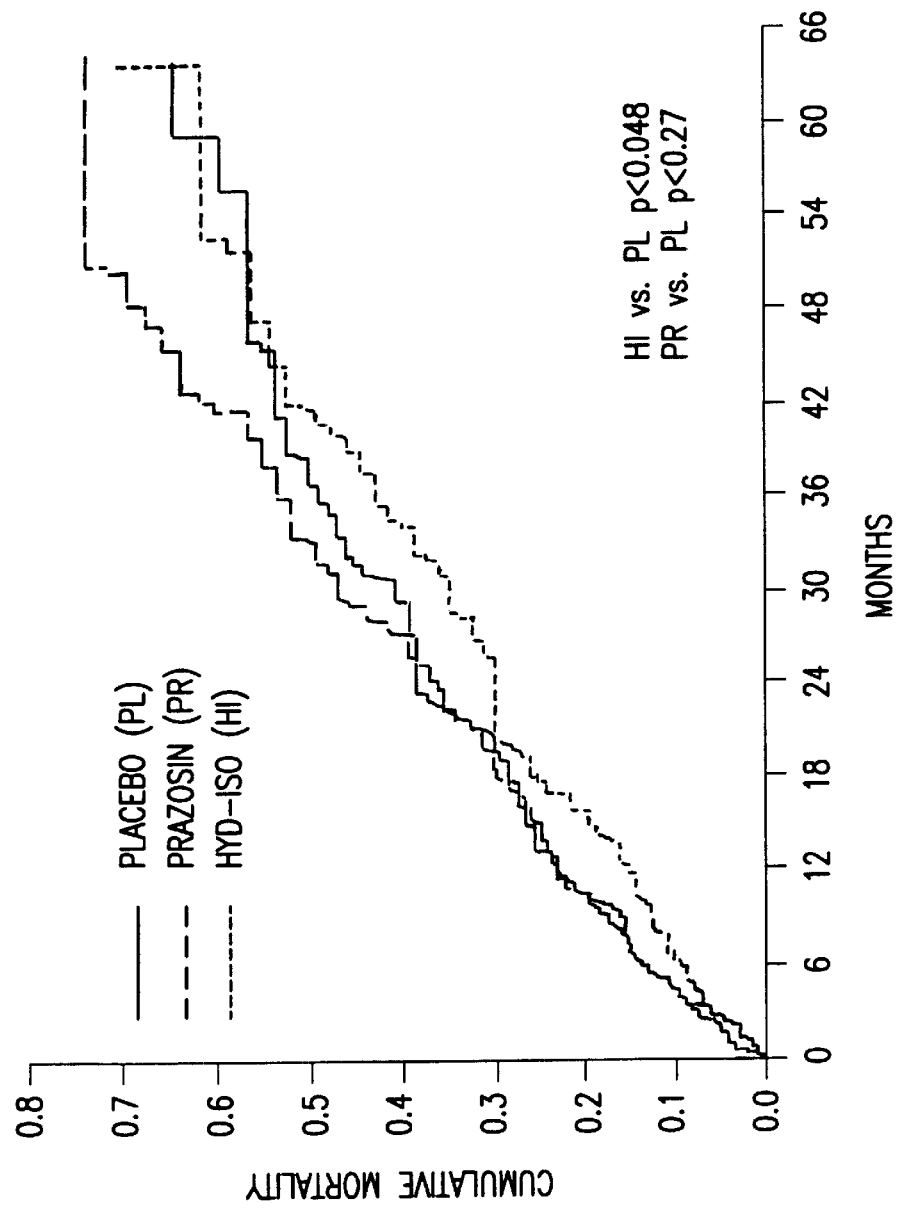

The placebo group mortality in V-HeFT I did not differ between white and black patients. There were 85 deaths among 192 white placebo patients (annual mortality rate [AMR] 18.8% and 35 deaths among 79 black placebo patients (AMR 17.3%) (p=NS) (FIG. 1). The inventors unexpectedly discovered that black patients exhibited a significant survival benefit in V-HeFT I from treatment with the combination of hydralazine and isosorbide dinitrate (FIG. 2A). There were 15 deaths among 49 black patients treated with the combination of hydralazine and isosorbide dinitrate (AMR 9.7%) compared to 35 of 79 patients in the placebo group (AMR 17.3%) (log-rank p=0.04). There were 21 deaths among 52 patients treated with prazosin (AMR 15.4) (p=NS compared to placebo). For white patients no treatment effect was demonstrated (FIG. 2B). Of 132 patients randomized to the combination of hydralazine and isosorbide dinitrate group, (AMR 22.1%) and 85 of 192 in the placebo group (AMR 18.8%) (p=NS). To further assess the relation between race and treatment with the combination of hydralazine and isosorbide dinitrate, and placebo, an interaction analysis was undertaken. This difference in congestive heart failure mortality corresponds to a risk ratio of 0.534 for mortality when comparing hydralazine and isosorbide dinitrate to placebo and was significant at p=0.043. The V-HeFT I mortality data were also analyzed after risk adjustment for differences in baseline characteristics. This adjustment further lowered the hydralazine and isosorbide dinitrate to placebo risk ratio to 0.341, p=0.004.

Figure 3B:
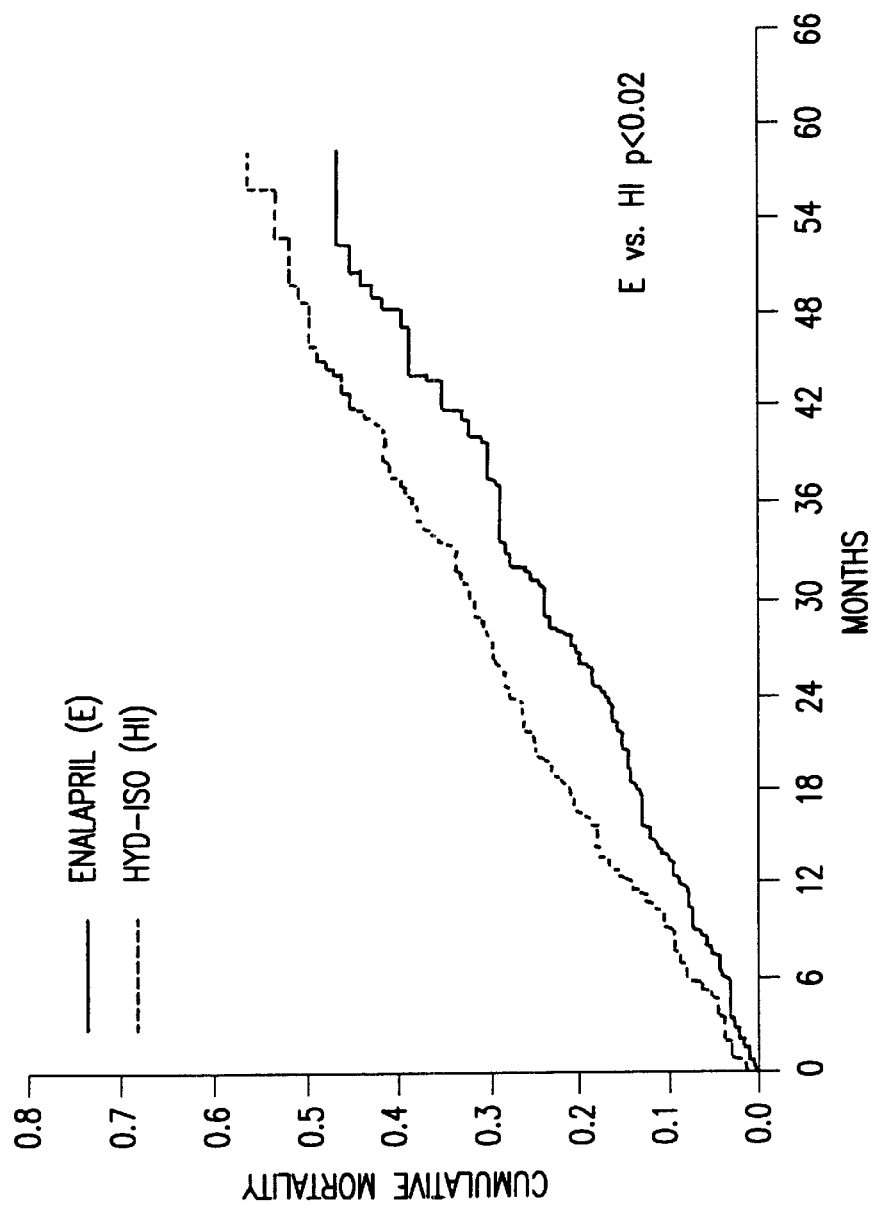
Figure 4A:
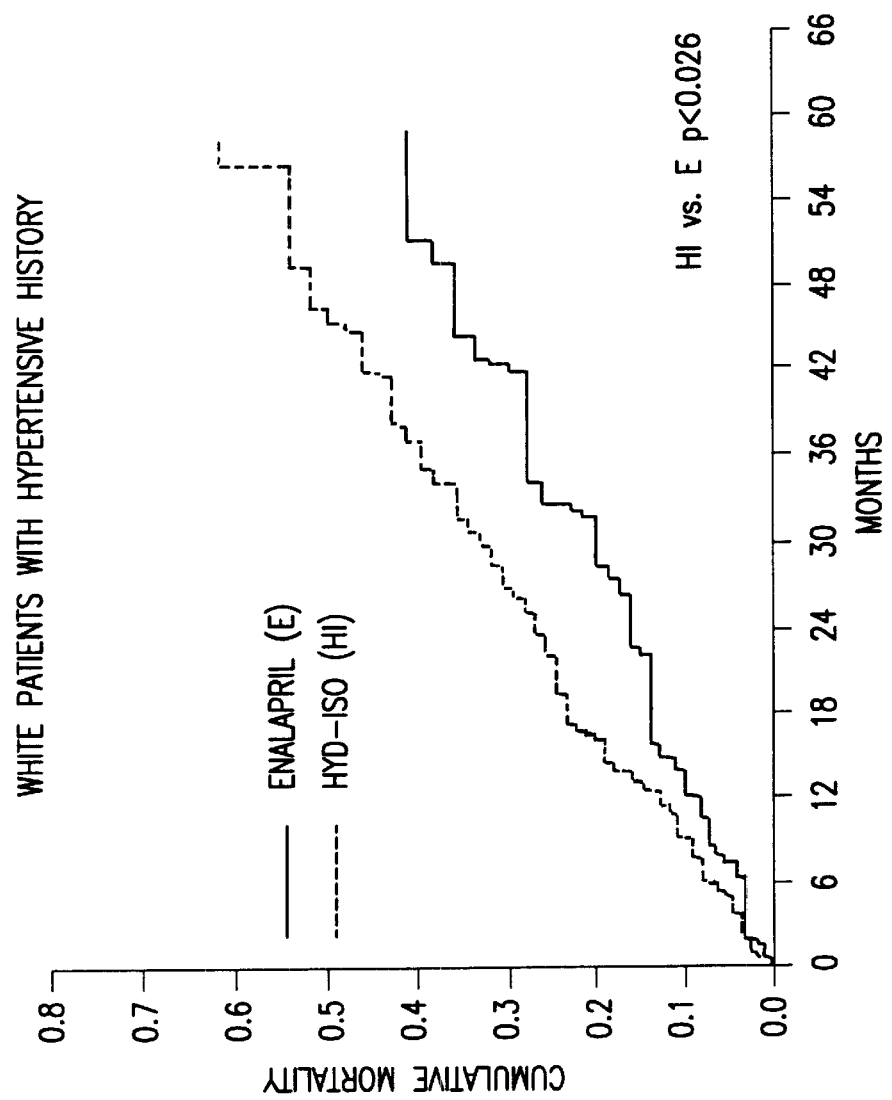
FIGS. 4A–4D demonstrates the influence of history of hypertension on the effect of therapy on survival in V-HeFT II.
Figure 4B:
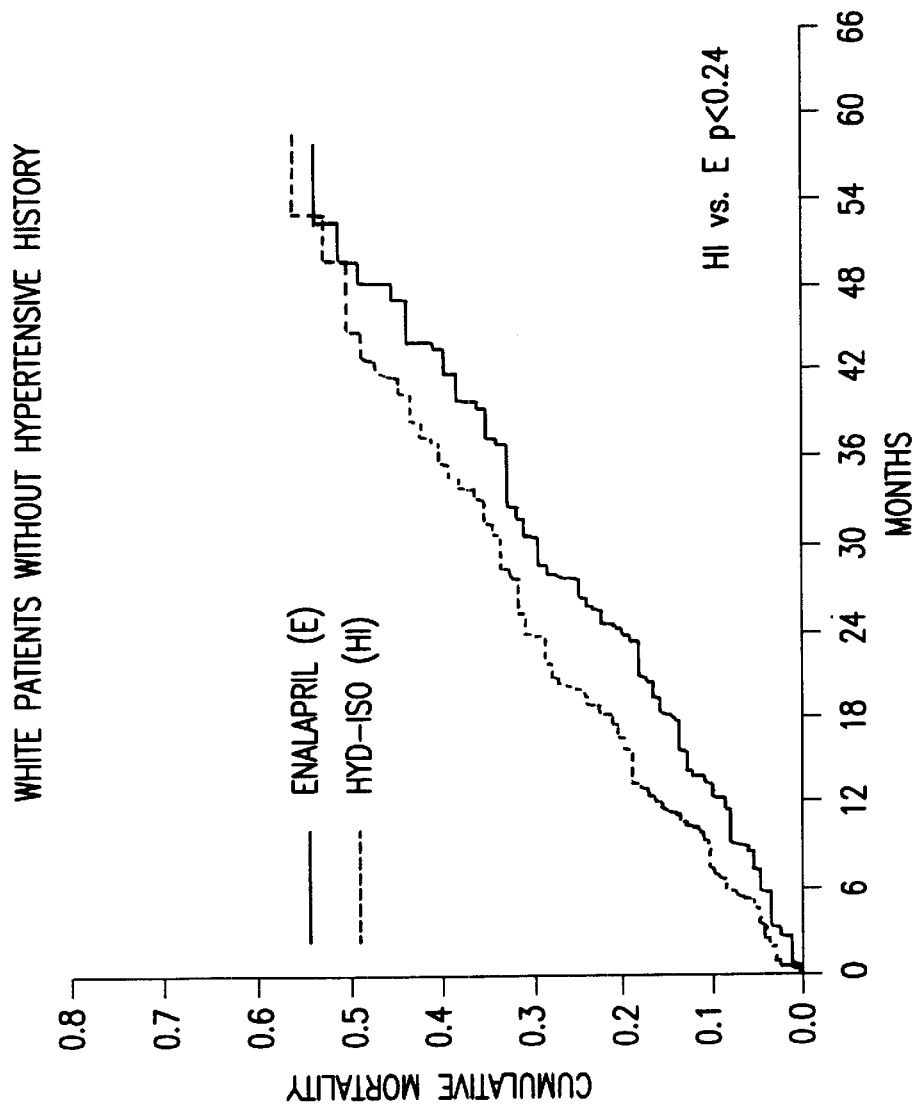
Figure 4C:
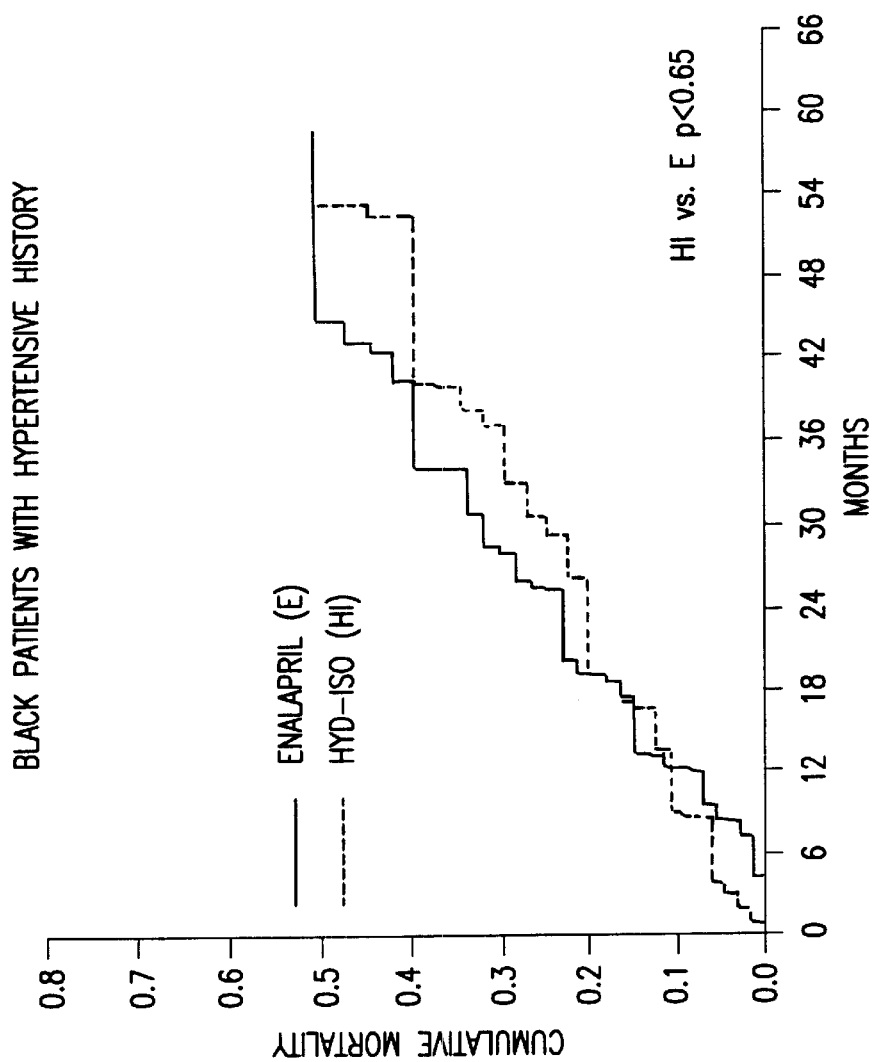
Figure 4D:
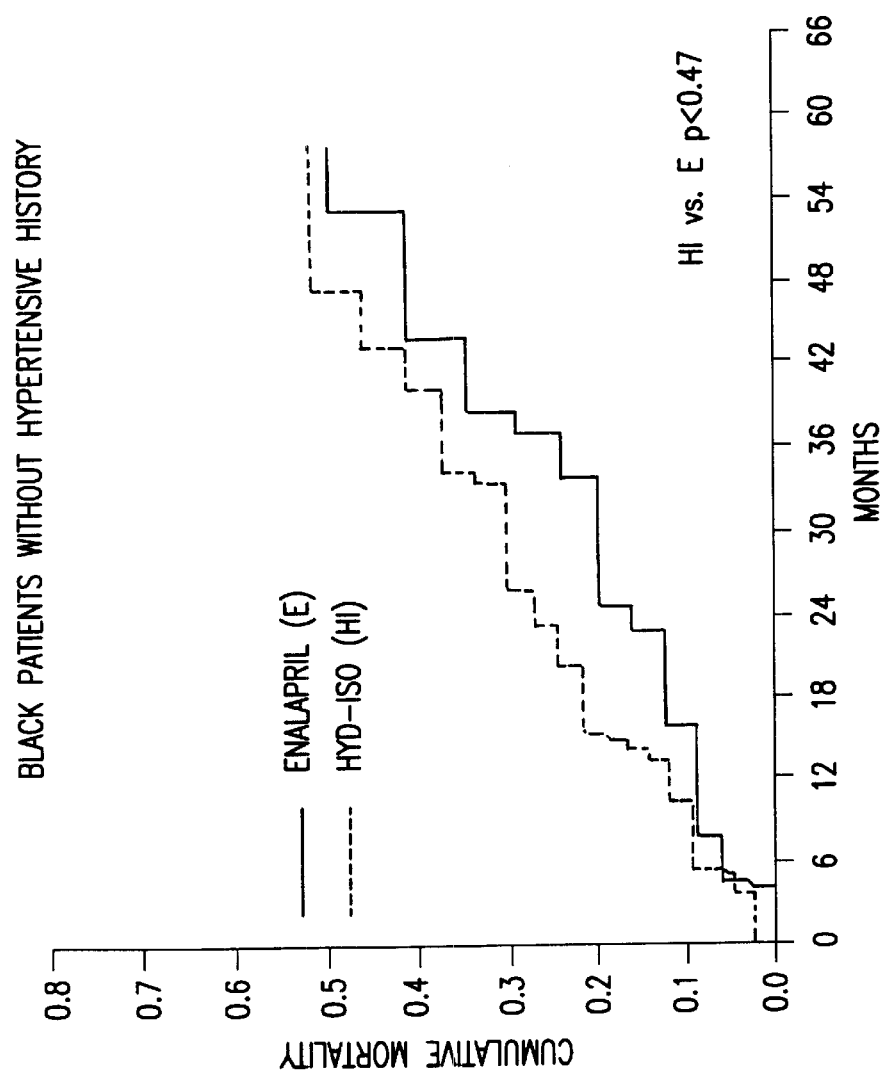

Cumulative mortality curves by treatment in V-HeFT II are shown in FIG. 3A and 3B. In the enalapril group, 39 of 106 black patients died (AMR 12.8%) compared to 39 of 109 black patients treated with the combination of hydralazine and isosorbide dinitrate, (AMR 12.9%) (p=NS). For white patients, 90 of 292 treated with enalapril died (AMR 11.0%) whereas 112 of 282 treated with the combination of hydralazine and isosorbide dinitrate died (AMR 14.9%) (log rank p=0.02). A trend for a significant interaction between race and treatment was demonstrated (p=0.09).

White patients with a history of hypertension had a significant mortality reduction with enalapril compared to the combination of hydralazine and isosorbide dinitrate, (p<0.02). Mortality reduction with enalapril did not differ in whites or blacks without hypertensive history or in blacks with hypertensive history (FIG. 4).

There was no difference in the number of patients hospitalized or the frequency of hospitalization for heart failure or all cause hospitalization between black and white patients or between treatment groups in either V-HeFT I or II (Table 4).

PHYSIOLOGIC CHANGES DURING FOLLOW-UP

In order to evaluate whether the race-related differences in outcome response to treatment were accompanied by differences in physiologic end-point responses, V-HeFT II data were analyzed regarding enalapril vs the combination of hydralazine and isosorbide dinitrate, effects on blood pressure, left ventricular ejection fraction, peak exercise oxygen consumption, PNE and radiographic CTR.

Figure 5:
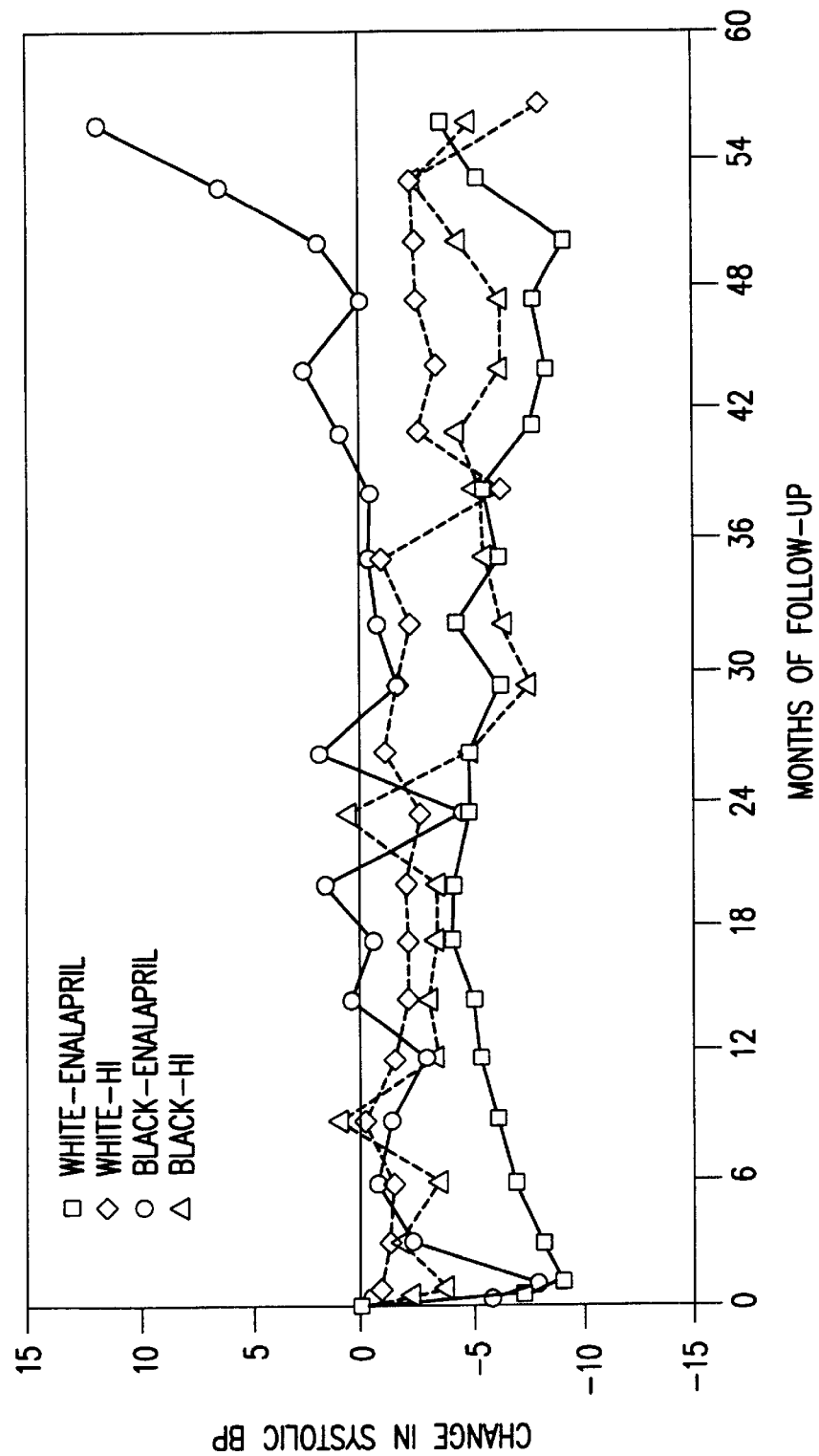
FIG. 5 shows the change in systolic blood pressure from pre-randomization level in V-HeFT II. Enalapril exerted a greater and more sustained blood pressure reduction in white than in black patients. The hydralazine-isosorbide dinitrate combination did not significantly reduce blood pressure in either racial group.

Blood Pressure (FIG. 5)

The initial fall in systolic blood pressure was greater in response to enalapril than to the combination of hydralazine and isosorbide dinitrate in both racial groups; however, blood pressure recovered by 13 weeks in the black patients and remained lower thereafter in the white patients during the 4.5 years of follow-up. The effect of the combination of hydralazine and isosorbide dinitrate, was statistically insignificant and similar in both racial groups.

Figure 6:
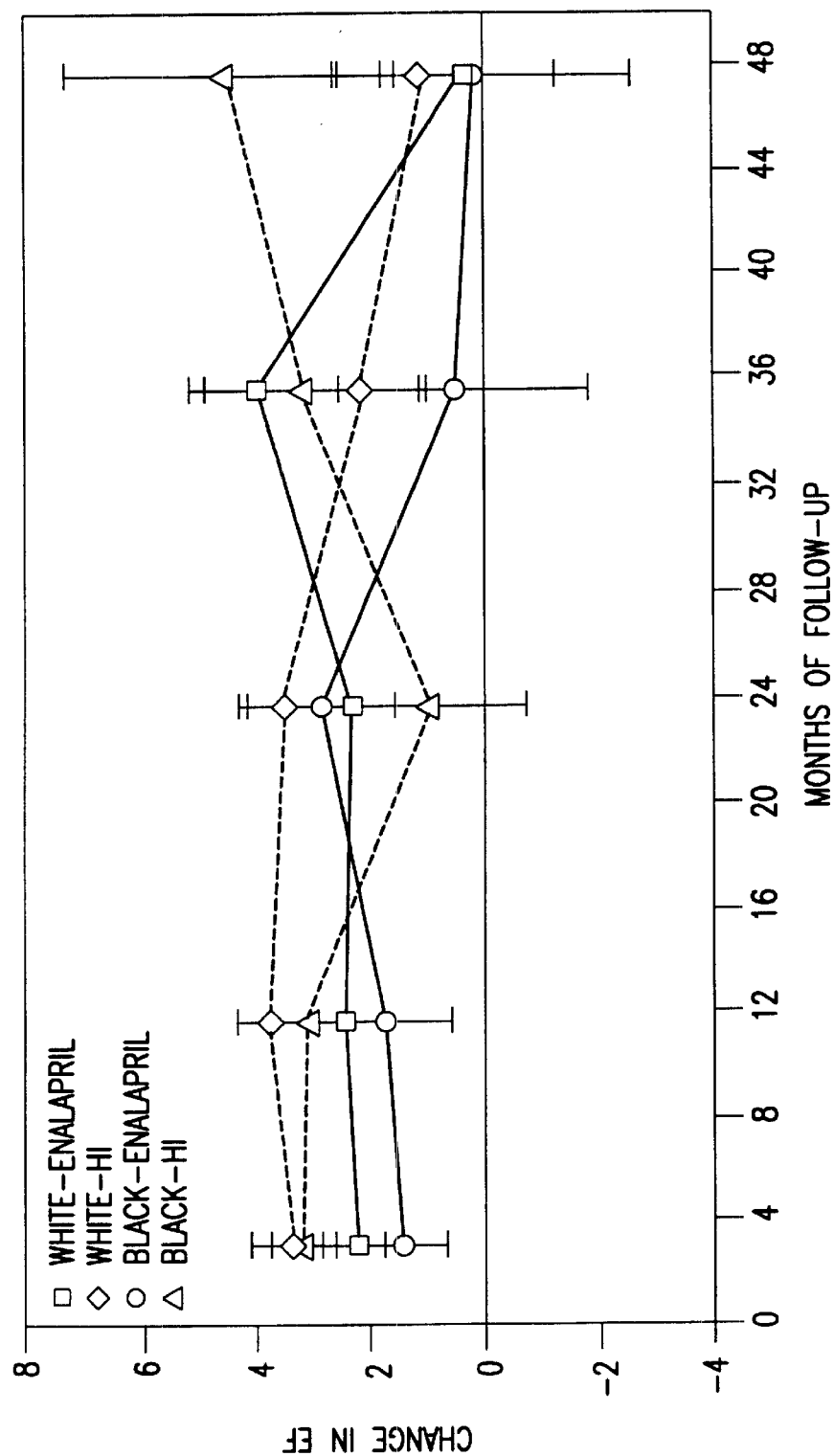
FIG. 6 shows the change in ejection fraction (EF) in V-HeFT II. EF tended to rise in all treatment groups; significant increases from baseline (p<0.05) are depicted by filled symbols. Increase of EF in black patients treated with enalapril tended to be less prominent.

Ejection Fraction (EF) (FIG. 6)

Radionuclide EF rose in response to both enalapril and the combination of hydralazine and isosorbide dinitrate in both racial groups. The increase for the first year in response to the combination of hydralazine and isosorbide dinitrate tended to be greater than to enalapril in both groups. Since survival was better in the white enalapril group, the magnitude of the late response may be influenced by survival of higher risk patients in that group.

Figure 7:
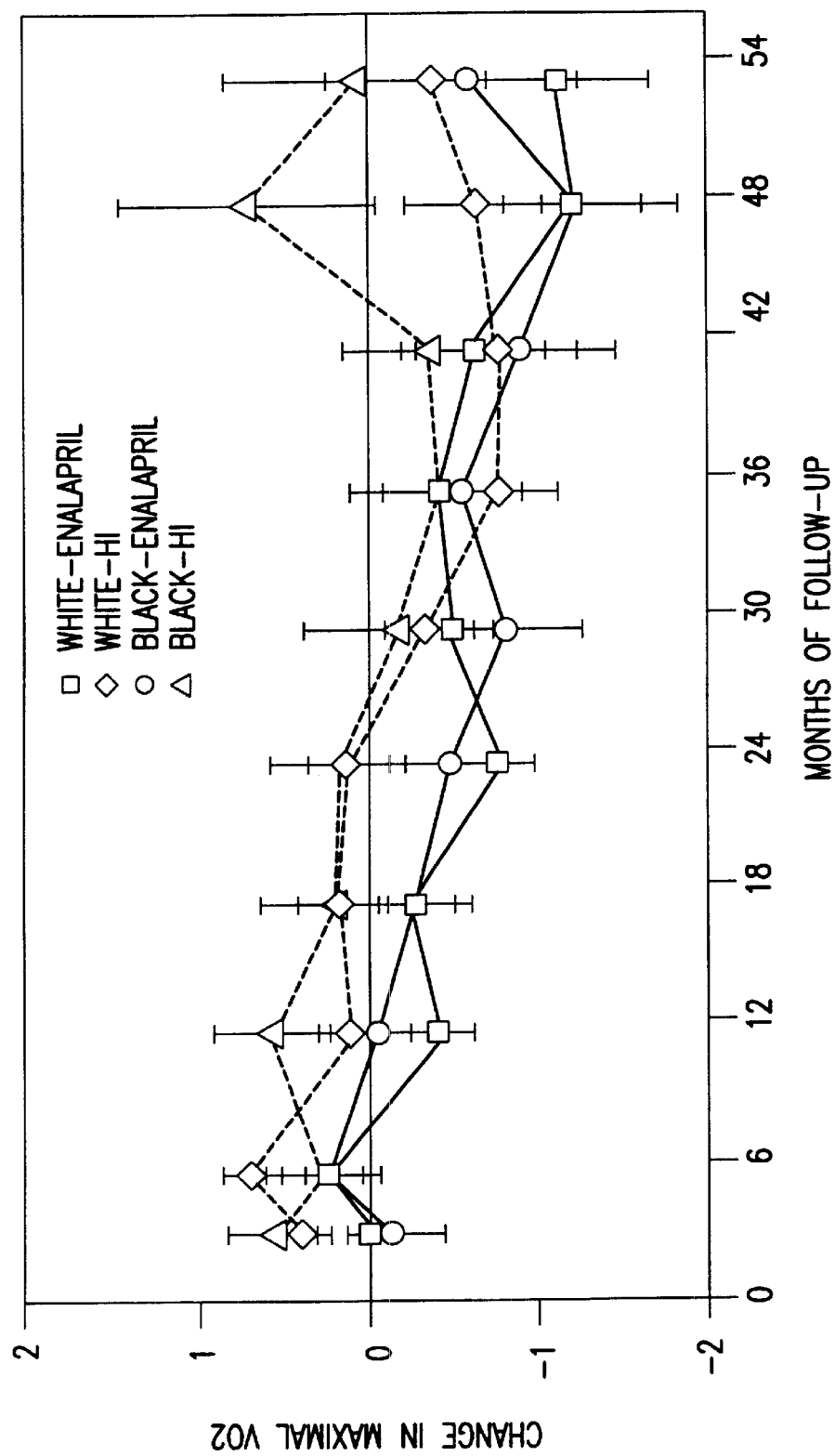
FIG. 7 shows the change in peak exercise oxygen consumption (maximal $VO_2$) in V-HeFT II. Hydralazine-isosorbide dinitrate produced an early (6 months) increase in exercise capacity and the enalapril group exhibited a more prominent decline in exercise capacity over time (1–4.5 years).

Exercise Tolerance ($MVO_2$) (FIG. 7)

Peak exercise oxygen consumption was monitored sequentially at 13 weeks and then at 6-month intervals throughout the study. Enalapril did not improve oxygen consumption ($MVO_2$) in either racial group whereas the combination of hydralazine and isosorbide dinitrate increased it in both black and white patients at 13 weeks. A comparison between the hydralazine and isosorbide dinitrate group and placebo group in V-HeHT I for the change from baseline in $MVO_2$ at 12 months approached statistical significance. Black patients on hydralazine and isosorbide dinitrate experienced a 0.962 ml/kg/min mean increase in $MVO_2$, whereas the patients on placebo experienced a 0.177 ml/kg/min decrease in $MVO_2$ over the same period, p=0.162. The corresponding values adjusted for baseline characteristics were 1.25 ml/kg/min increase for hydralazine and isosorbide dinitrate and a 0.394 ml/kg/min decrease for placebo, p=0.068. Longitudinal models were fit to examine $MVO_2$ differences over the first year of V-HeFT I. These models indicated a similar trend as above, with black patients on hydralazine and isosorbide dinitrate having greater $MVO_2$ than black patients on placebo, p=0.11. Hydralazine and isosorbide dinitrate clinically and statistically improved exercise tolerance as assessed by $MVO_2$.

There was a significant difference in the effects of hydralazine and isosorbide dinitrate and enalapril on the response to the Heart Condition Assessment (HCA) questionnaire on quality of life in black patients in V-HeFT II. Hydralazine and isosorbide dinitrate progressively improved quality of life scores in black patients, attaining a value of −0.67 at 12 months. Over the same period enalapril worsened quality of life scores, up to a value of +1.04. This difference was significant, p=0.043.

The surrogate endpoint of $MVO_2$ at 12 months differed significantly between the hydralazine and isosorbide dinitrate group and the enalapril group. Black patients on hydralazine and isosorbide dinitrate experienced a 0.602 ml/kg/min mean improvement from baseline in $MVO_2$ versus a 0.047 ml/kg/min decrease for enalapril, p=0.19. Following adjustment for differences in baseline characteristics, black patients on hydralazine and isosorbide dinitrate experienced a 0.787 ml/kg/min mean improvement from baseline in $MVO_2$ versus a 0.010 ml/kg/min increase for enalapril patients, p=0.15. $MVO_2$ was also analyzed using a longitudinal model that took into account all $MVO_2$ data collected over the entire 12 months. In this analysis, hydralazine and isosorbide dinitrate performed better than enalapril from baseline, p=0.084 unadjusted and p=0.067 risk-adjusted. The improvement in exercise tolerance associated with hydralazine and isosorbide dinitrate, as measured by $MVO_2$, is clinically significant and approaches statistical significance.

Figure 8:
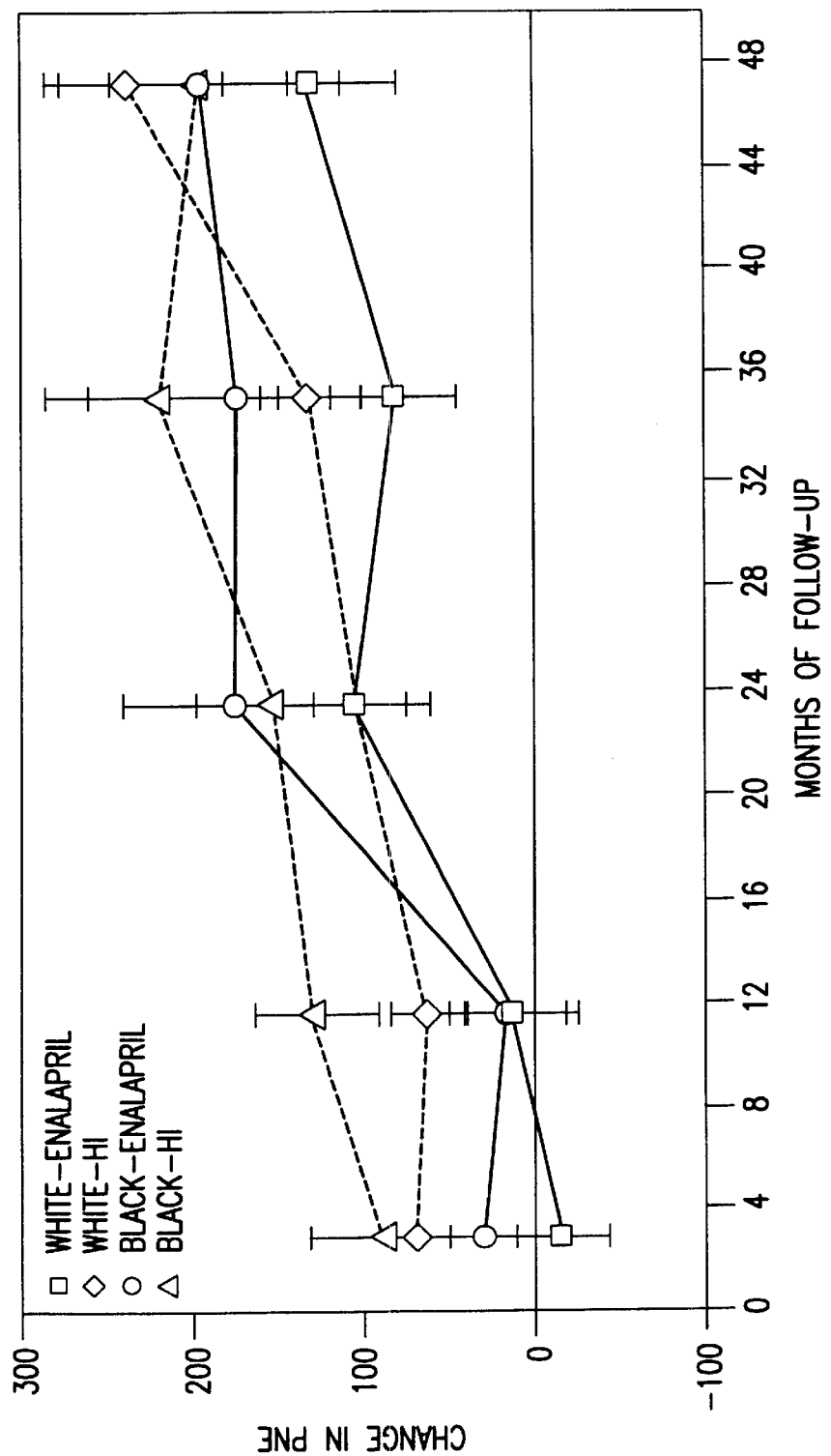
FIG. 8 shows the change in plasma norepinephrine (PNE) in V-HeFT II. Norepinephrine rose in the first year in response to hydralazine-isosorbide in both racial groups but not in the enalapril groups. Thereafter PNE increased similarly in all treatment groups.

Plasma Norepinephrine (FIG. 8)

The increase in PNE observed in response to the combination of hydralazine and isosorbide dinitrate, was not apparent in response to enalapril in either racial group. No racial difference in response was detected.

Figure 9:
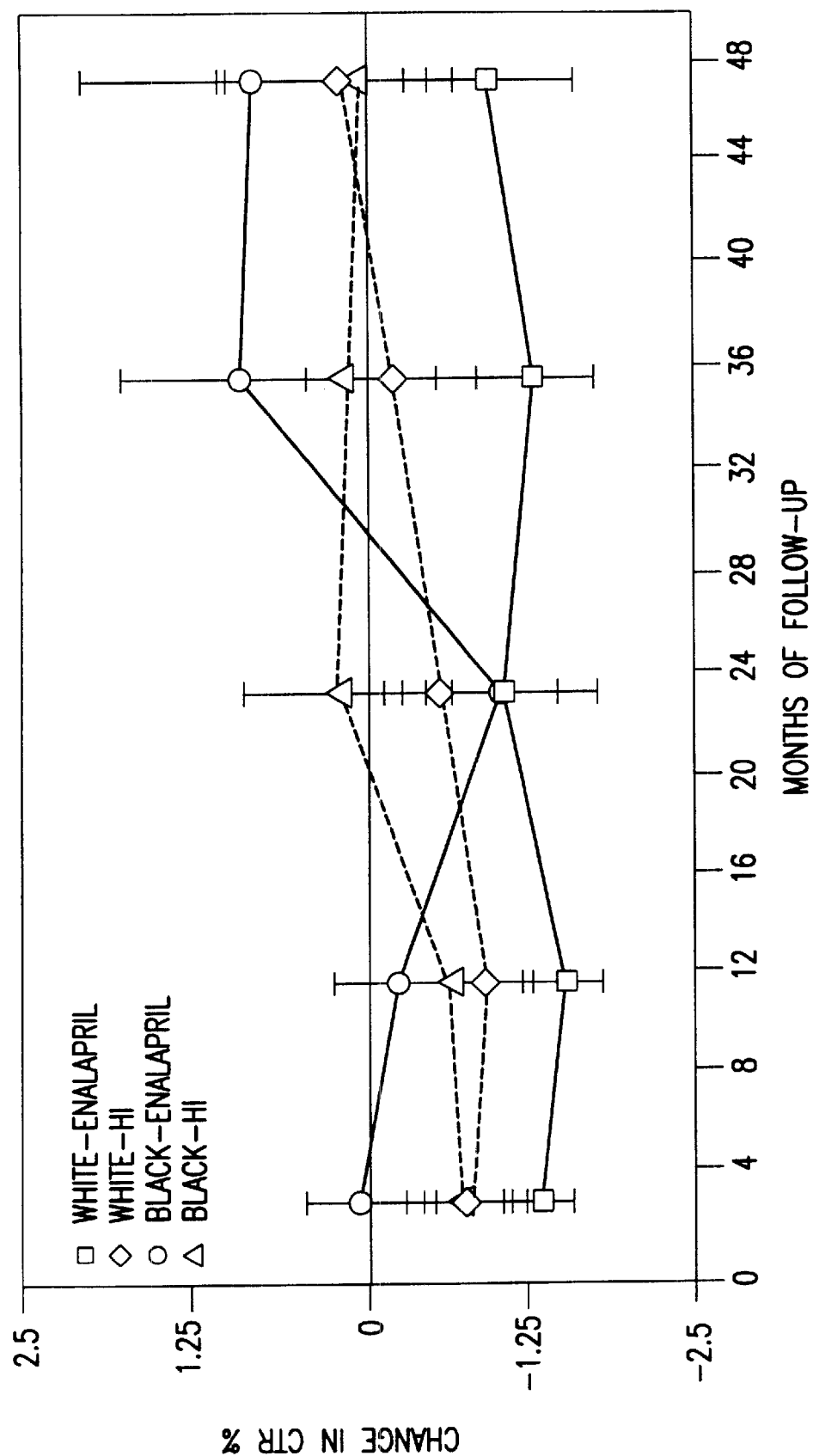
FIG. 9 shows the change in cardiothoracic ratio in (CTR) in V-HeFT II. Significant sustained reduction was apparent only in white patients treated with enalapril.

Cardiothoracic Ratio (FIG. 9)

A significant reduction in radiographic heart size was noted during follow-up in white patients in both treatment groups. The beneficial effect of enalapril persisted through 3 years whereas the benefit of the combination of hydralazine and isosorbide dinitrate was no longer significant after the first year. Black patients exhibited no significant heart size reduction with either treatment.

DISCUSSION

In the present invention, the inventors analyzed data from V-HeFT I and V-HeFT II to determine whether there was a significant baseline difference between black and white patients with heart failure, and to determine whether race has an impact on mortality reduction, oxygen consumption, exercise tolerance and quality of life observed with vasodilator and ACE inhibitor therapy. It has now been discovered that the combination of at least one hydralazine compound and at least one of isosorbide dinitrate and isosorbide mononitrate, and, optionally, one or more compounds, such as, for example, a digitalis, a diuretic compound, and/or a compound used to treat cardiovascular diseases has an unexpectedly superior effect in prolonging survival and improving oxygen consumption, exercise tolerance and quality of life in black patients. This combination is equally effective as enalapril in this subgroup. In contrast, enalapril exhibits its more favorable effect on survival particularly in the white population.

Since V-HeFT I compared the combination of hydralazine and isosorbide dinitrate to placebo and V-HeFT II compared enalapril and the combination of hydralazine and isosorbide dinitrate, without a placebo arm, it is not possible to determine whether the racial influence on the mortality reduction from ACE inhibitors is due to a reduced effect of ACE inhibitors in the black population or a greater response to the combination of hydralazine and isosorbide dinitrate in that population. The non-sustained blood pressure reduction observed in response to enalapril in the black population compared to the white population suggests that at least some of the differential outcome response to V-HeFT II can be attributed to lesser ACE inhibitor effect in black patients.

Although not addressed, the data clearly suggest less efficacy of enalapril in the black subgroup than in the white subgroup, with a black:white relative risk of 1.15 in the placebo group and 1.34 in the enalapril group. Nonetheless, the evidence now discovered from V-HeFT I of the unique and superior efficacy of the combination of hydralazine and isosorbide dinitrate in the black population suggests that this racial difference in efficacy also contributed to the similar effects of ACE inhibitor and the combination of hydralazine and isosorbide dinitrate in the black patients.

It is important to examine the baseline differences between black and white patients to explore the possible interaction of these differences on the response to therapy. As noted in previous studies, blacks had a lower incidence than whites of CAD (Peniston et al, *J. Am. Coll. Cardiol.*, 299A (1994); Joint National Committee, *Arch Intern Med*, 144:1045–1057 (1985)), and a higher incidence of prior hypertension. point National Committee, *Arch. Intern. Med.*, 144:1045–1057 (1985); Bourassa et al, *J. Am. Coll. Cardiol.*, 22(Suppl A):14–19 (1993)). In V-HeFT, blacks demonstrated a larger radiographic cardiothoracic ratio and a non-significant trend for a higher ejection fraction, and the ejection fraction was significantly higher in blacks than in whites with a hypertensive history, the group in whom the racial differences in response to ACE inhibition was most prominent. Although we cannot exclude that baseline differences in the prevalence of diastolic dysfunction or other variables could have contributed to the apparent racial differences in response, prior analysis has demonstrated a similar response to therapy in subgroups based on etiology, hypertension history, cardiothoracic ratio and ejection fraction (Cohn et al, *Circulation*, (Suppl VI); 75:49–54 (1987); Johnson et al, *Circulation*, 87(Suppl VI): 32–39 (1993).

The finding that mortality and morbidity as represented by CHF hospitalizations are similar in blacks and whites with heart failure is at variance with previous reports. Ghali et al (*Arch. Intern. Med.*, 150:769–773 (1990)) reported that non-white men were more commonly hospitalized for heart failure. In a previous analysis Ghali et al (*Arch. Intern. Med.*, 148:2013–2106 (1988)) had indicated that uncontrolled hypertension was present in 44% of non-white patients whereas 64% were non-compliant with medications. Alexander et al (*JAMA*, 274(13):1037–1042 (1995)) analyzed an Health Maintenance Organization (HMO) database and found that black males and females were at greater risk of CHF hospitalization; however in males this excess risk could largely be accounted for by clinical variables including hypertension. Bourassa et al (*J. Am. Coll, Cardiol.*, 22(Suppl A):14–19, 1993)) also reported from the SOLVD Registry that blacks had a greater incidence of hospitalization, but a similar mortality to that in whites. In contrast, the National Center for Health Statistics in the United States (*N. Engl. J. Med.*, 329:621–627 (1993)) reported higher age adjusted death rates for blacks compared to whites between 1970 and 1985, a time period largely before the SOLVD and V-HeFT trials were conducted.

The present invention addresses a much different population. Hypertension, often uncontrolled, was common in the Ghali and Alexander databases whereas currently hypertensive patients were excluded from V-HeFT. Patients were closely followed in V-HeFT by protocol, usually by the same investigator team. The follow-up certainly differed from the large population database retrospectively examined by Ghali and Alexander as well as from the SOLVD Registry. A plausible explanation is that when access to resources is equal and there is close follow-up, no difference in mortality or hospitalizations will be observed between blacks and whites.

Neurohormonal Mechanisms

Prior studies in hypertension have suggested that reduced responsiveness to ACE inhibitors may be attributed to a lower PRA in the black population. Indeed, the differential benefit in V-HeFT II of ACE inhibitor therapy in whites compared to blacks was particularly prominent in those with a prior history of hypertension in whom PRA was significantly lower in blacks than in whites.

The mechanism of PRA stimulation in heart failure remains controversial. Diuretics, which were being administered chronically in nearly all the patients, may be partly responsible for the renin stimulation, (Cody et al, *J. Clin. Invest.*, 77:1441–1452 (1986)) but PRA values were elevated in untreated patients as well. (Anand et al, *Circulation*, 78:II-106 (1988). Why black patients with heart failure and a hypertensive history exhibit less renin response than their white counterparts remains uncertain but is consistent with previous observations of less renin response to furosemide in the black population. (Kaplan et al, *Annals of Internal Medicine*, 84:639–645 (1976)). It is also unclear why PRA was not lower in the black than the white heart failure population without a history of hypertension, but this observation raises interesting speculations about a possible genetic difference between black individuals with and without a history of hypertension.

The slightly lower PNE level in black compared to white patients in V-HeFT II has not previously been noted in a heart failure population. The difference could reflect a less severe heart failure syndrome in blacks and their EF, an important determinant of survival, (Cohn et al, Circulation, 87(Suppl VI):5–16 (1993)) was significantly higher. Nonetheless, the similar mortality observed in the two racial subgroups does not support the hypothesis that blacks were less sick. Previous data indicate that plasma epinephrine in black adults and urinary norepinephrine in black children are lower than in whites (Mills et al, Hypertension, 25:88–91 (1995); Pratt et al, J. Hypertension, January 10:93–96 (1992)). Mills et al (Hypertension, 25:88–91 (1995)) also reported that blacks had increased beta receptor number and sensitivity which could account for lower circulating levels. How these observations apply to patients with heart failure, whose sympathetic nervous system is stimulated by a variety of afferent signals, remains uncertain.

Implications of Differential Response to Therapy

The differential pharmacologic response that has now been discovered between black and white patients from V-HeFT is consistent with the previously described differential antihypertensive effects, with blacks less responsive to ACE inhibitors (Br. J. Clin. Pharmac., 14(Suppl S):97–101 (1982); Saunders et al, Arch. Intern Med., 150:1710–1713 (1990)) and beta blockers (JAMA, 248:1996–2003 (1982); JAMA, 248:2004–2011 (1982)). When compared to the effect of the combination of hydralazine and isosorbide dinitrate, the greater mortality reduction in V-HeFT with ACE inhibitors in whites than in blacks raises the possibility that surveys of heart failure outcome in ACE inhibitor-treated patients might reveal a poorer prognosis in the black population.

Without intending to be bound by any theory of the invention, reduced efficacy of ACE inhibitors in blacks appears to be related in part to a less active renin-angiotensin system in blacks. This observation is consistent with the concept of Cody et al (Hypertension, 5 (Suppl III):36–42, (1983)) that PRA activity is predictive of ACE inhibitor efficacy in both hypertension and heart failure. A racial difference in the effect of ACE inhibitors on blood pressure also was confirmed in this study in patients with heart failure. No clear evidence of a racial difference in effect on other physiologic end-points was observed, perhaps because of the modest sample size; but the benefits of enalapril on PNE and CTR appeared to be most prominent in the white population.

The unexpected finding of the present invention is that blacks responded more favorably than whites to the combination of at least one hydralazine compound and either isosorbide dinitrate or isosorbide mononitrate. As this combination exerted a mortality effect similar to that of enalapril in V-HeFT II, it raises important considerations. Hydralazine was initially combined with isosorbide dinitrate because of their additive hemodynamic effects (Pierpont et al., Chest, 73:8–13 (1978)). Recent evidence, however, supports an antioxidant effect of hydralazine to enhance and sustain the efficacy of nitrates (Bauer et al., Circulation, 84:35–39 (1991); MAnzel et al., J. Clin. Invest., 98:1465–1470 (1996); Gogia et al., J. Am. Coll. Cardiol. 26:1575–1580 (1995)). The uniquely favorable effect of this combination in black patients suggests the possibility that blacks, particularly those with a hypertensive history, may have a greater deficiency of nitric oxide generation that is restored by the isosorbide dinitrate and/or isosorbide mononitrate. Similarly, the apparent lesser efficacy of enalapril in this subgroup suggests that the renin-angiotensin system may not be playing as active a role in the black hypertensive population.

The present finding of a consistency of observations of a racial difference in response in V-HeFT I and V-HeFT II, buttressed by the apparent racial difference in response in SOLVD and the racial difference in blood pressure response in V-HeFT II, support the suggestion that therapy for heart failure, improved oxygen consumption, exercise tolerance and quality of life might appropriately be racially tailored. ACE inhibitors remain the treatment of choice to prolong survival in white patients. The present inventors now discovered that for black patients the combination of at least one hydralazine compound and at least one of isosorbide dinitrate and isosorbide mononitrate is an attractive alternative, since it exerted unexpectedly superior improvement in exercise tolerance, quality of life, oxygen consumption and EF and unexpectedly prolonged survival.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention without departing from the spirit and scope thereof.

TABLE 1

V-HeFT I - BASELINE VARIABLES

|  | Black (n = 180) | White (n = 480) |
|---|---|---|
| Demographics: |  |  |
| Age (years) | 56.3 ± 9.0 | 59.2 ± 6.9** |
| CAD (%) | 20.8 | 53.2** |
| Hx HTN (%) | 46.6 | 37.3 |
| Measurements |  |  |
| SBP sitting (mmHg) | 118.0 ± 16.4 | 119.7 ± 19.6 |
| DBP sitting (mmHg) | 76.6 ± 9.6 | 75.6 ± 10.3 |
| Heart Rate sitting (beats/min) | 83.1 ± 13.1 | 81.7 ± 13.3 |
| Ejection Fraction (%) | 31.3 ± 14.1 | 29.3 ± 12.4 |
| MVO$_2$ (ml/kg/min) | 14.7 ± 4.3 | 14.7 ± 3.6 |
| Cardiothoracic Ratio (%) | 55.0 ± 6.3 | 52.7 ± 6.3** |

All values are means (±standard deviation).
** = P < 0.01; * = P < 0.05 Black vs White
CAD = coronary artery disease; hx HTN = history of hypertension;
SBP = systolic blood pressure; DBP = diastolic blood pressure;
MVO$_2$ = maximal oxygen consumption

TABLE 2

HeFT II - BASELINE VARIABLES

|  | Black (n = 215) | White (n = 574) |
|---|---|---|
| Demographics: |  |  |
| Age (years) | 58.8 ± 9.0 | 61.1 ± 8.0 |
| CAD (%) | 28.4 | 61.6** |
| Hx HTN (%) | 64.9 | 41.5** |
| Measurements: |  |  |
| SBP sitting (mmHg) | 126.0 ± 16.6 | 126.4 ± 17.3 |
| DBP sitting (mmHg) | 79.4 ± 9.4 | 77.7 ± 9.3 |
| Ejection Fraction (%) | 29.2 ± 11.5 | 29.0 ± 11.1 |
| MVO$_2$ (ml/kg/min) | 13.4 ± 3.4 | 13.9 ± 3.5* |
| Cardiothoracic Ratio (%) | 54.3 ± 6 | 52.2 ± 6* |
| PNE (pg/ml) | 449 (330–602) | 504 (368–693)+** |
| PRA (ng/ml/hr) | 6.6 (3.4–12.7) | 7.3 (3.9–17.7)+ |

**P < 0.01; *P < 0.05 Black vs White; + = median values (1st–3rd quartile)
All other values are means (± standard deviation).
PNE = plasma norepinephrine; PRA = plasma renin activity

TABLE 3

BASELINE CHARACTERISTICS

|  | W (+HTN) (218) | W (−HTN) (318) | B (+HTN) (132) | B (−HTN) (72) |
|---|---|---|---|---|
| PRA ng ml$^{-1}$ hr$^{-1}$ | 8.1 (4–18.2)† | 6.8 (3.8–16.1) | 6.2 (3.3–12.7) | 7.0 (4.6–15.8) |
| PNE | 497 (366–659) | 510 (373–729) | 469 (329–601) | 437 (333–621) |
| EF % | 31 ± 11.8‡ | 27.6 ± 10.4 | 30.7 ± 12‡ | 26.6 ± 10.4 |
| CTR | 0.52 ± 0.06 | 0.52 ± 0.06 | 0.54 ± 0.06 | 0.54 ± 0.06 |
| MVO$_2$ ml kg$^{-1}$ min$^{-1}$ | 13.6 ± 3.3 | 14 ± 3.6 | 13.6 ± 3.5 | 12.7 ± 3.3 |
| SBP mmHg | 133 ± 17‡ | 122 ± 15 | 129 ± 17‡ | 121 ± 15 |
| DBP mmHg | 80 ± 9† | 75 ± 9 | 81 ± 10‡ | 77 ± 9 |

† = $P < 0.02$ vs. Blacks (+HTN); ‡ = $P < 0.02$ vs Whites (−HTN) or Blacks (−HTN); +HTN = with hypertension; −HTN = without hypertension; EF = ejection fraction; CTR = cardiothoracic ratio

TABLE 4

HOSPITALIZATION

V-HeFT I

| | White | | | | Black | | | | |
|---|---|---|---|---|---|---|---|---|---|
| n (%) | Placebo | Prazosin | Hyd-Iso | Total | Placebo | Prazosin | Hyd-Iso | Total | White vs. Black |
| Number of patients hospitalized for CHF (%) | 49 (25.5) | 40 (31.5) $P = 0.24$ | 32 (24.2) $P = 0.80$ | 121 (26.8) | 16 (20.3) | 12 (23.) $P = 0.70$ | 11 (22.4) $P = 0.77$ | 39 (21.7) | $P = 0.18$ |
| Number of patients hospitalized for any reason (%) | 67 (34.9) | 45 (35.4) $P = 0.93$ | 56 (42.4) $P = 0.17$ | 168 (37.3) | 39 (49.4) | 21 (40.4) $P = 0.32$ | 20 (40.8) $P = 0.35$ | 80 (44.4) | $P = 0.10$ |

V-HeFT II

| | White | | | Black | | | |
|---|---|---|---|---|---|---|---|
| n (%) | Hyd-Iso | Enalapril | Total | Hyd-Iso | Enalapril | Total | White vs. Black |
| Number of patients hospitalized for CHF | 51 (18.1) | 51 (17.5) | 102 (17.8) $P = 0.85$ | 23 (21.1) | 24 (22.6) | 47 (21.9) $P = 0.79$ | $P = 0.20$ |
| Number of patients hospitalized for any reason | 165 (58.5) | 181 (62.0) | 346 (60.3) $P = 0.40$ | 59 (54.1) | 65 (61.3) | 124 (57.7) $P = 0.29$ | $P = 0.51$ |

What is claimed is:

1. A method of reducing mortality associated with heart failure, for improving the oxygen consumption, for improving the quality of life or for improving exercise tolerance in a black patient comprising administering to the black patient a therapeutically effective amount of at least one hydralazine compound of Formula (I) or a pharmaceutically acceptable salt thereof, and at least one of isosorbide dinitrate and isosorbide mononitrate, wherein the hydralazine compound of Formula (I) is

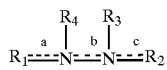

(I)

wherein a, b and c are each independently a single or a double bond; $R_1$ and $R_2$ are each independently a hydrogen, an alkyl, an ester or a heterocyclic ring; $R_3$ and $R_4$ are each independently a lone pair of electrons or a hydrogen, with the proviso that at least one of $R_1$, $R_2$, $R_3$ and $R_4$ is not a hydrogen.

2. The method of claim 1, wherein the black patient has a less active renin-angiotensin system relative to a white patient.

3. The method of claim 1, wherein the black patient has hypertension.

4. The method of claim 1, further comprising administering a pharmaceutically acceptable carrier.

5. The method of claim 1, wherein the hydralazine compound is budralazine, cadralazine, dihydralazine, endralazine, hydralazine, pildralazine, todralazine or a pharmaceutically acceptable salt thereof.

6. The method of claim 5, wherein the hydralazine compound is hydralazine hydrochloride.

7. The method of claim 6, wherein the hydralazine hydrochloride is administered in an amount of about 30 milligrams per day to about 300 milligrams per day.

8. The method of claim 1, wherein the isosorbide dinitrate is administered in an amount of about 20 milligrams per day to about 200 milligrams per day.

9. The method of claim 1, wherein the isosorbide mononitrate is 25 administered in an amount of about 10 milligrams per day to about 120 milligrams per day.

10. The method of claim 1, comprising administering at least one hydralazine compound or a pharmaceutically acceptable salt thereof and isosorbide dinitrate.

11. The method of claim 1, comprising administering at least one hydralazine compound or a pharmaceutically acceptable salt thereof and isosorbide mononitrate.

12. The method of claim 1, comprising administering at least one hydralazine compound or a pharmaceutically acceptable salt thereof, isosorbide dinitrate and isosorbide mononitrate.

13. The method of claim 1, wherein the at least one hydralazine compound and the at least one of isosorbide dinitrate and isosorbide mononitrate are administered orally.

14. The method of claim 13, wherein the at least one hydralazine compound and the at least one of isosorbide dinitrate and isosorbide mononitrate are orally administered in the form of a solid dose.

15. The method of claim 14, wherein the solid dose is in the form of a tablet or a capsule.

16. The method of claim 15, wherein the capsule is in the form of a sustained release capsule.

17. The method of claim 15, wherein the tablet is in the form of a sublingual tablet, a sustained-release tablet or a chewable tablet.

18. The method of claim 1, wherein the at least one hydralazine compound and the at least one of isosorbide dinitrate and isosorbide mononitrate are administered to the black patient as components of the same composition.

19. The method of claim 1, wherein the at least one hydralazine compound and the at least one of isosorbide dinitrate and isosorbide mononitrate are administered to the black patient as separate components.

20. The method of claim 19, wherein the at least one hydralazine compound and the at least one of isosorbide dinitrate and isosorbide mononitrate are administered to the black patient as separate components at about the same time.

21. The method of claim 1, further comprising administering a digitalis.

22. The method of claim 21, wherein the digitalis is digoxin.

23. The method of claim 22, wherein the digoxin is administered in an amount to achieve a blood serum concentration of at least about 0.7 nanograms per milliliter to about 2.0 nanograms per milliliter.

24. The method of claim 1, further comprising administering an effective edema managing amount of a diuretic compound.

25. The method of claim 24, wherein the diuretic compound is a thiazide, ethacrynic acid, a furosemide, a spiranolactone, a triamterene or a mixture thereof.

26. The method of claim 24, further comprising administering potassium.

27. The method of claim 26, wherein the potassium is administered in the form of potassium chloride or by the daily ingestion of foods with high potassium content.

28. The method of claim 1, further comprising administering at least one compound used to treat a cardiovascular disease.

29. The method of claim 28, wherein the at least one compound used to treat a cardiovascular disease is an angiotensin-converting enzyme inhibitor, a beta-adrenergic blocker, a cholesterol reducer, a calcium channel blocker, an angiotensin II receptor antagonist, an endothelin antagonist, or a mixture thereof.

30. The method of claim 29, wherein the angiotensin-converting enzyme inhibitor is alacepril, benazepril, captopril, ceronapril, cilazapril, delapril, enalapril, enalaprilat, fosinopril, imidapril, lisinopril, moveltipril, pentopril, perindopril, quinapril, ramipril, rentiapril, spirapril, temocapril, trandolapril, zofenopril, or a mixture thereof.

31. The method of claim 30, wherein the angiotensin-converting enzyme inhibitor is enalapril.

32. A method of reducing the incidence of mortality associated with chronic congestive heart failure in a patient with impaired cardiac function and concomitant reduced exercise tolerance, comprising orally administering to said patient between about 30 and about 300 milligrams of hydralazine hydrochloride per day, and at least one of (i) between about 20 and about 200 milligrams of isosorbide dinitrate, per day, and (ii) between about 10 and about 120 milligrams of isosorbide mononitrate, per day wherein the improvement comprises administering the hydralazine hydrochloride and the at least one of isosorbide dinitrate and isosorbide mononitrate to a black patient.

33. The method of claim 32, further comprising treating the black patient orally with digoxin in an amount sufficient to achieve a blood serum concentration of digoxin of at least about 0.7 nanograms per milliliter and an effective edema managing amount of at least one pharmaceutically acceptable diuretic selected from a thiazide, a ethacrynic acid, a furosemide, a spironalactone and a triamterene.

34. The method of claim 33, further comprising administering potassium.

35. The method of claim 32, further comprising treating the black patient with at least one compound used to treat a cardiovascular disease.

36. The method of claim 35, wherein the at least one compound used to treat a cardiovascular disease is an angiotensin-converting enzyme inhibitor, a beta-adrenergic blocker, a cholesterol reducer, a calcium channel blocker, an angiotensin II receptor antagonist, an endothelin antagonist, or a mixture thereof.

37. The method of claim 36, wherein the angiotensin-converting enzyme inhibitor is alacepril, benazepril, captopril, ceronapril, cilazapril, delapril, enalapril, enalaprilat, fosinopril, imidapril, lisinopril, moveltipril, pentopril, perindopril, quinapril, ramipril, rentiapril, spirapril, temocapril, trandolapril, zofenopril, or a mixture thereof.

38. The method of claim 37, wherein the angiotensin-converting enzyme inhibitor is enalapril.

39. The method of claim 1, wherein the black patient is not as responsive to an angiotensin-converting enzyme inhibitor relative to a white patient.

40. The method of claim 1, wherein the black patient has a deficient nitric oxide generation system.

41. The method of claim 32, wherein the black patient is not as responsive to an angiotensin-converting enzyme inhibitor relative to a white patient.

42. The method of claim 32, wherein the black patient has a deficient nitric oxide generation system.

43. The method of claim 32, wherein the black patient has a less active renin-angiotensin system relative to a white patient.

44. The method of claim 32, wherein the black patient has hypertension.

45. A method of reducing mortality associated with heart failure in a black patient comprising administering to the black patient a therapeutically effective amount of hydralazine or a pharmaceutically acceptable salt thereof and isosorbide dinitrate.

46. A method of reducing mortality associated with heart failure in a black patient with hypertension comprising administering to the black patient with hypertension a therapeutically effective amount of hydralazine or a pharmaceutically acceptable salt thereof and isosorbide dinitrate.

47. The method of claim 32, wherein the hydralazine hydrochloride and the at least one of isosorbide dinitrate and isosorbide mononitrate are administered orally.

48. The method of claim 47, wherein the hydralazine hydrochloride and the at least one of isosorbide dinitrate and isosorbide mononitrate are orally administered in the form of a solid dose.

49. The method of claim 48, wherein the solid dose is in the form of a tablet or a capsule.

50. The method of claim 49, wherein the capsule is in the form of a sustained release capsule.

51. The method of claim 49, wherein the tablet is in the form of a sublingual tablet, a sustained-release tablet or a chewable tablet.

52. The method of claim 32, wherein the hydralazine hydrochloride and the at least one of isosorbide dinitrate and isosorbide mononitrate are administered to the black patient as components of the same composition.

53. The method of claim 32, wherein the hydralazine hydrochloride and the at least one of isosorbide dinitrate and isosorbide mononitrate are administered to the black patient as separate components.

54. The method of claim 53, wherein the hydralazine hydrochloride and the at least one of isosorbide dinitrate and isosorbide mononitrate are administered to the black patient as separate components at about the same time.

* * * * *

UNITED STATES PATENT AND TRADEMARK OFFICE
CERTIFICATE OF CORRECTION

PATENT NO.       : 6,465,463 B1
APPLICATION NO.  : 09/658261
DATED            : October 15, 2002
INVENTOR(S)      : Cohn and Carson It is certified that error appears in the above-identified patent and that said Letters Patent is hereby corrected as shown below:

Drawing Figs 2A - Figs 2B should be,

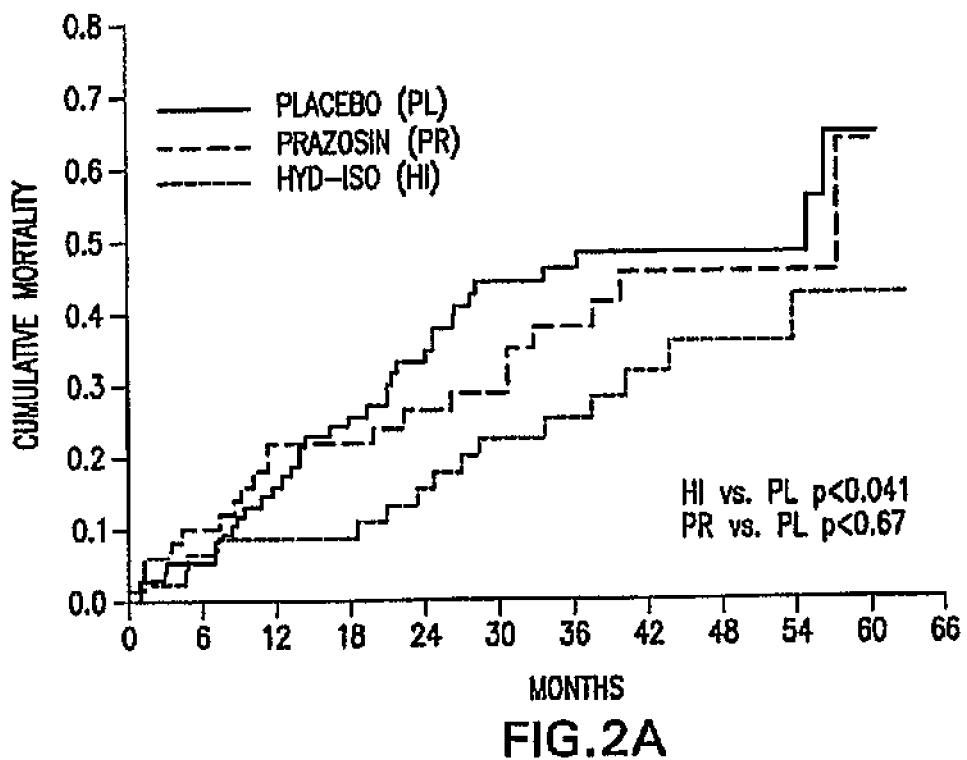

FIG.2A

UNITED STATES PATENT AND TRADEMARK OFFICE
CERTIFICATE OF CORRECTION

PATENT NO.        : 6,465,463 B1
APPLICATION NO. : 09/658261
DATED             : October 15, 2002
INVENTOR(S)       : Cohn and Carson It is certified that error appears in the above-identified patent and that said Letters Patent is hereby corrected as shown below:

Drawing Figs 2A - Figs 2B should be, (cont'd)

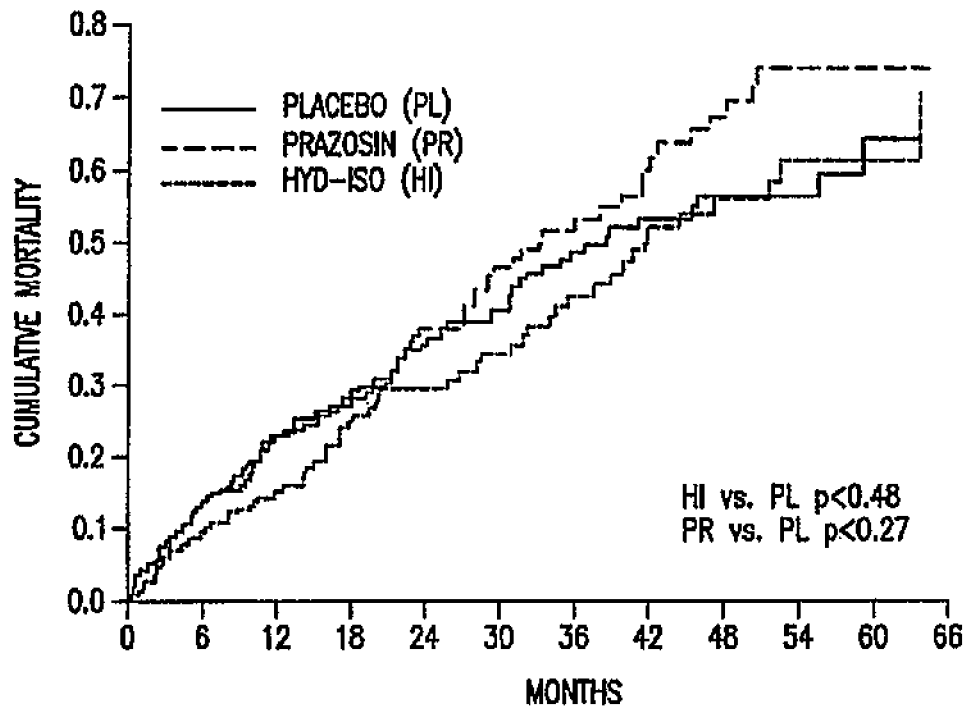

FIG.2B

Signed and Sealed this

Second Day of October, 2007

JON W. DUDAS
*Director of the United States Patent and Trademark Office*